United States Patent

Lindemann et al.

[11] 4,215,064
[45] Jul. 29, 1980

[54] PHOSPHOBETAINES

[75] Inventors: Martin K. O. Lindemann, Bridgewater; Raymond L. Mayhew, Summit; Anthony J. O'Lenick, Jr., Fairlawn; Robert J. Verdicchio, Succasunna, all of N.J.

[73] Assignees: Johnson & Johnson, New Brunswick; Mona Industries, Inc., Paterson, both of N.J.

[21] Appl. No.: 965,461

[22] Filed: Nov. 30, 1978

[51] Int. Cl.² .................... A23J 7/00; C07F 9/02; C11C 3/00
[52] U.S. Cl. .................... 260/403; 260/944; 260/945; 260/943; 424/70; 252/356; 252/357; 252/110; 252/524; 252/526; 252/527; 252/528; 544/157; 548/336; 548/341
[58] Field of Search .............. 260/403, 944, 945, 943; 424/70; 252/356, 357; 544/157

[56] References Cited

U.S. PATENT DOCUMENTS

| | | | |
|---|---|---|---|
| 3,856,893 | 12/1974 | Diery et al. | 260/945 |
| 3,928,509 | 12/1975 | Diery et al. | 260/945 |
| 3,950,417 | 4/1976 | Verdicchio et al. | 424/70 |
| 3,962,418 | 8/1976 | Birkofer | 424/70 |
| 4,181,634 | 1/1980 | Kennedy et al. | 252/545 |

*Primary Examiner*—John F. Niebling
*Attorney, Agent, or Firm*—Steven P. Berman

[57] ABSTRACT

Phosphobetaine Compounds of the formula

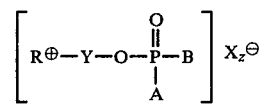

wherein
A is selected from $O^-$, OM and $-O-Y-R+$
B is selected from $O^-$ and $OM^-$
$X^-$ is an anion
Z is an integer from 0 to 2 with the proviso that only one of A and B can be $O^-$ and Z is of a value necessary for charge balance and R is an amidoamine reactant moiety.

19 Claims, No Drawings

PHOSPHOBETAINES

BACKGROUND OF THE INVENTION

The present invention relates to novel compositions of matter consisting of specific betaine derivatives referred to hereinafter as "phosphobetaines". More particularly, this invention relates to novel amphoteric and zwitterionic betaine surfactants having at least one phosphorus-containing anion in the molecule.

Betaines and certain substituted betaines are known in the art but prior to the present invention the novel phosphobetaines of this invention had not been disclosed or suggested. The phosphobetaines of the present invention exhibit outstanding foaming, viscosity-building, wetting, cleansing, detergency, anti-static and emulsifying properties and are therefore useful in industrial applications calling for high performance surface active agents. The compounds are also highly stable species and are extremely well tolerated by human tissue, i.e., they exhibit exceptionally low ocular irritation and oral toxicity, and are therefore eminently suited and useful as surface active agents in personal care compositions.

THE INVENTION

The novel phosphobetaine compounds of the invention may be represented by the following general formula:

$$\left[ R^{\oplus}-Y-O-\overset{\overset{O}{\|}}{\underset{A}{P}}-B \right] X_z^{\ominus} \quad (I)$$

wherein

A is selected from $O^-$, OM, and $-O-Y-R^{\oplus}$

B is selected from $O^-$ and OM'

$X^{\ominus}$ is an anion z is an integer from 0 to 2 with the proviso that only one of A and B can be $O^-$ and z is of a value necessary for charge balance (i.e., when A and B are $O^-$ and OM', or OM and $O^-$, respectively, z is 0; when A and B are OM and OM', or $-O-Y-R^{\oplus}$ and $O^-$, respectively, z is 1; when A is $-O-Y-R^{\oplus}$ and B is OM', z is 2), R is an amidoamine reactant moiety of the formula $$\left[ R^1-\overset{\overset{O}{\|}}{C}-\overset{\overset{R^2}{|}}{N}-(CH_2)_n-\overset{\overset{R^3}{|}}{\underset{R^4}{N}}- \right]^{\oplus}$$

wherein $R^1$ is alkyl, alkenyl, alkoxy, or hydroxyalkyl of from 5 to 22 carbon atoms each, or aryl or alkaryl of up to 20 carbon atoms, $R^2$ is hydrogen or alkyl, hydroxyalkyl or alkenyl of up to 6 carbon atoms each or cycloalkyl of up to 6 carbon atoms, preferably of from 2 to 5 carbon atoms, or polyoxyalkalene of up to 10 carbon atoms, $R^3$ and $R^4$, which may be the same or different, are selected from alkyl, hydroxyalkyl, carboxyalkyl of up to 6 carbon atoms in each alkyl moiety, and polyoxyalkylene of up to 10 carbon atoms; in addition, $R^3$ and $R^4$ taken together with the nitrogen to which they are attached, may represent an N-heterocycle, e.g., a morpholino structure, in which the Y radical is bonded to a ring atom of said N-heterocycle other than the nitrogen of the R moiety;

n is an integer from 2 to 12.

The term "polyoxyalkalene radical" as used above in the definition of $R^2$, $R^3$ and $R^4$ may be of the formula $(R^5-O-R^{5'})_m$, wherein $R^5$ and $R^{5'}$ are alkyl of from 1 to 4 carbon atoms and m is an integer from about 2 to 10.

In addition to the foregoing definitions wherein R is amidoamine,

R may be an N-heterocyclic radical which may contain one additional hetero atom (e.g., oxygen, sulfur or another nitrogen) and contains 5 to 6 total ring carbon atoms; optionally said heterocyclic radical may be substituted with alkyl and/or hydroxyalkyl of up to 20 carbon atoms each. Typical of such N-heterocyclic radicals are imidazolyl, N-alkylmorpholino, alkyl-pyrimidino, alkyloxazolinyl, and the like. Such compounds may be represented by the formula $$\begin{array}{c}
R_6 \\
| \\
N \\
/ \quad \diagdown \\
(CH_2)_o \quad (CH_2)_p \\
\diagdown \quad / \\
Z
\end{array} \quad \text{with } R^1$$

wherein

Z is N, S or O;

o is an integer from 0 to 3;

p is an integer from 1 to 3; provided that the sum of o+p is from 3 to 4;

$R^1$ is defined as before and is linked to a ring carbon atom; and $R_6$ is alkyl of from 2 to 6 carbon atoms which may be substituted with a hydroxyl group at the terminal or a non-terminal carbon atom.

Y may be alkylene, optionally interrupted by up to 3 oxygen atoms, of up to 12 carbon atoms, which alkylene chain may optionally be substituted with lower alkyl, alkoxy, hydroxy or hydroxyalkyl, e.g., of not more than 10 carbon atoms each.

M and M', which may be the same or different, are (a) hydrogen, (b) an organic radical selected from alkyl or hydroxyalkyl of up to 6 carbon atoms, polyhydroxyalkyl of up to 10 carbon atoms, glyceryl, cycloalkyl of up to 6 carbon atoms, aryl or arylalkyl of up to 10 carbon atoms, or (c) a salt radical selected from alkali metals (e.g., sodium or potassium), alkaline earth metals (e.g., magnesium or calcium), and mono-, di-, or tri-ethanolamine. With reference to formula(III) below, wherein both M and M' are contained, there is the proviso that when either M or M' is an organic radical (b), the other of M and M' must be hydrogen or a salt radical (c).

Particularly preferred sub-groups of the compounds of formula I can be represented as follows:

$$\overset{+}{R}-Y-O-\overset{\overset{O}{\|}}{\underset{O^-}{P}}-OM \quad (II)$$

$$\left[ \overset{+}{R}-Y-O-\overset{\overset{O}{\|}}{\underset{OM''}{P}}-OM \right] X^- \quad (III)$$

-continued

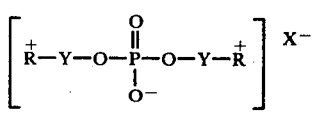

The compounds of general formula IV are bis-phosphobetaines containing two amine moieties. Compounds III and IV require the presence of an anion (X⁻) for charge balance. Said X⁻ radical can be an anion such as hydroxy or a halide, sulfate, phosphate, or a negatively charged (anion) radical supplied by a solvent or a reactant used in the synthesis of compounds of formulas III and IV. For instance, X⁻ may be the halide moiety ("Hal") released in the reactions below.

The phosphobetaine compounds (I) of the invention can be prepared from the corresponding phosphate esters and amine reactants, as follows:

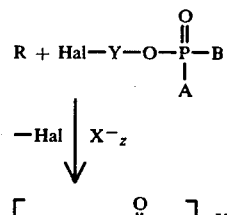
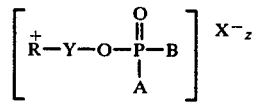

wherein
R is an amine reactant of the formulas

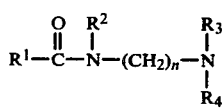

or

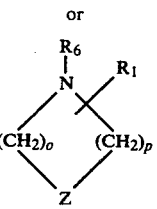

in which the radicals are defined as above.

More specifically, the respective groups of phosphobetaine compounds of the invention as set forth above under formulas II, III and IV can be synthesized by a number of processes which are set forth schematically below:

Process A (Amine + Phosphate Ester Halide)

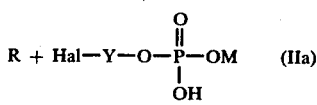

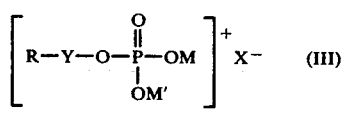

wherein Hal = halogen and the other radicals are defined as above

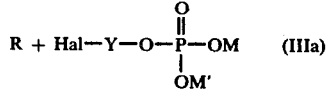

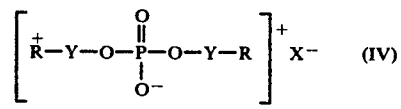

wherein the radicals are defined as above;

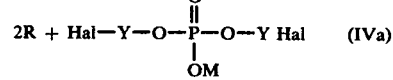

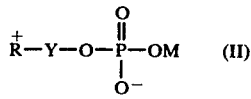

wherein the radicals are defined as above.

An alternate process for making certain of the inventive phosphobetaine compounds utilizes a novel reaction between the amine reactant (R) and a cyclic hydroxypropylene-containing phosphate ester reactant, as shown schematically below:

Process B (Amine + Cyclic Phosphate Ester)

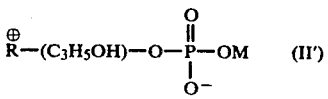

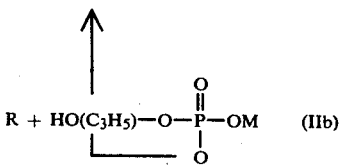

-continued

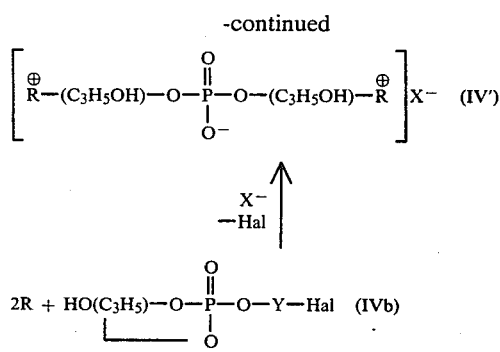

wherein the reactants are defined as before, it being understood that the anion X$^-$ can be supplied by the halide (Hal) group which is split from reactant IIIb (in which case X$^-$=Hal) or from another source, as explained above. The designations "HO(C$_3$H$_5$)" or "(C$_3$H$_5$OH)" herein refer to a hydroxypropylene function in which the hydroxy can be linked to any one of the three carbons and the cyclic oxa- moiety is linked to one of the three carbons, probably at the 3- or 2- position of the propyl group.

The reactants required in the processes can be prepared as follows:

Preparation of Intermediate "R" Reactants

The amine reactant "R" applicable to all of the syntheses, is, in general, prepared by reacting an acid with an aminoalkyl-substituted tertiary amine to result in the amidoamine function. Alternatively, an acid can be reacted with an aminoalkyl-substituted secondary amine, followed by further treatment of the reaction product with alkylene oxide. Finally, when R represents the N-heterocyclic structure, e.g., imidazolyl, this can be prepared in accordance with known techniques, e.g., as taught in U.S. Pat. No. 2,267,965.

Reaction (7) below yields the non-cyclic reactants "R" and Reaction (8) illustrates the preparation of a typical cyclic amine reactant R (Imidazolyl):

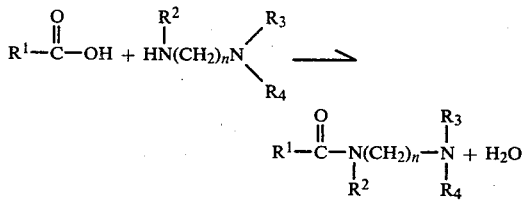

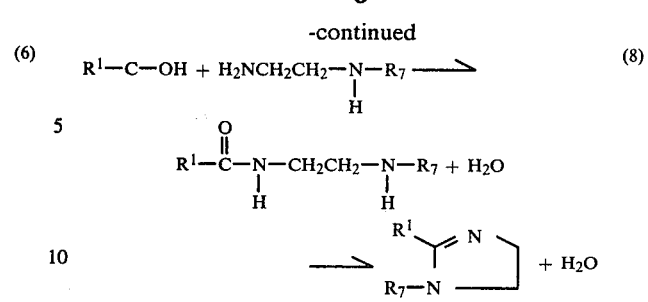

wherein, R$^1$ is defined as above and R$^7$ is alkyl of 2 to 6 carbon atoms which may be substituted with a hydroxyl group (at the terminal or a non-terminal carbon atom. This cyclic reactant can be prepared as disclosed in U.S. Pat. No. 2,267,965.

Preparation of Phosphate Ester Intermediate Reactants

The preparation of the phosphate ester intermediate reactants as set forth in reaction sequences 1, 2 and 3 above are also prepared by reactions which are illustrated as follows:

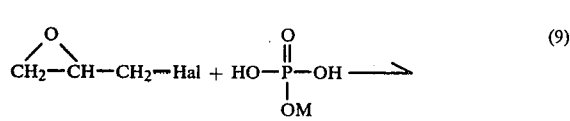

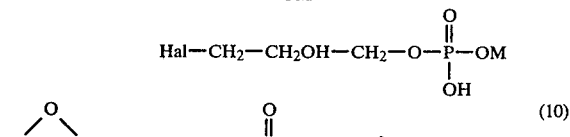

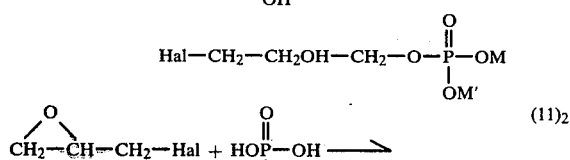

For certain reactants IIa, viz., those wherein M is hydrogen or an alkali or alkaline earth metal cation, the following intermediate synthesis can be used:

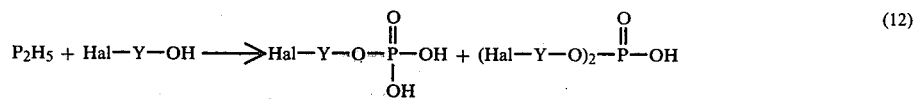

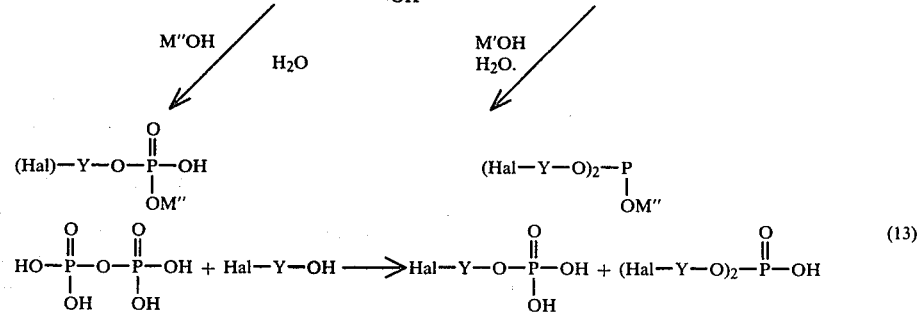

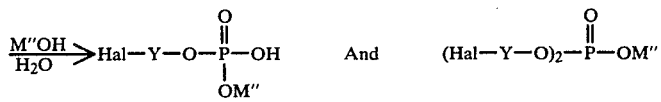 And 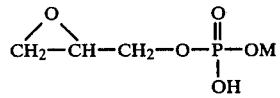

wherein

M'' is an alkali or alkaline earth metal salt cation (e.g., sodium, potassium, magnesium or calcium)

Reactions (12) and (13) are carried out in two steps. The first is conducted under anhydrous conditions to generate a-chloro phosphate. Subsequently, this material is diluted to 40% with water and one mole equivalent of M''OH, e.g., sodium hydroxide.

The phosphate ester intermediate reactants required for synthesis route (B) supra, can be prepared as follows:

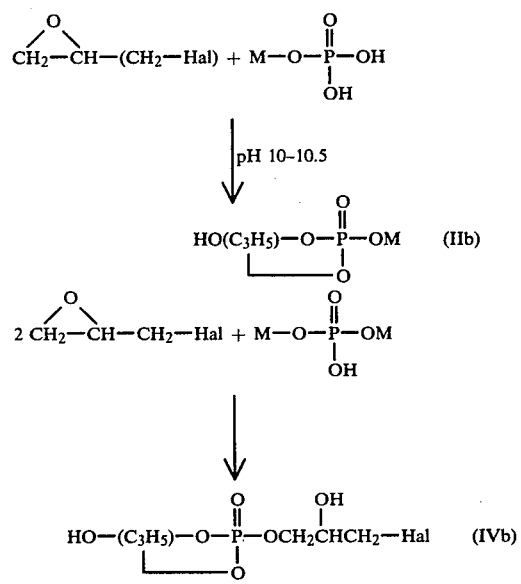

It will be noted that Reactions (14) and (15) utilize reactants similar to the reactants needed in Reactions 10 and 11 supra (although with the more limited hydroxypropyl definition), but that different, cyclic, products are obtained. The different products are the result of a different pH adjustment; thus, while reaction 10 is carried out at a pH of about 4–5, reaction 11 is carried out at a pH of 9.5 to 10.5, resulting in a cyclic product. This cyclic product may contain also some vicinal epoxy material so that the formula

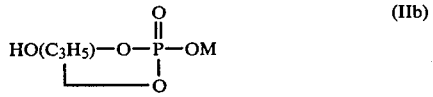 (IIb)

should be understood as including not only one or more of the isomers resulting from linkage of the oxa-oxygen to any one of the hydroxy-propylene carbons (to make a 5-, or 6-membered ring) but also the following structure:

$$CH_2-CH-CH_2-O-P(=O)(OM)-OH$$ (with epoxide on left)

Operation at a higher pH, e.g., 10.5 or higher, would favor formation of the vicinal epoxy-containing material.

In carrying out the reactions 1 to 4 as set forth above leading to the ultimate phosphobetaine compound of the invention, the amine intermediate reactant (R) is reacted with the appropriate phosphate ester intermediate reactant and these reactions are generally carried out in an aqueous system at 80°–100° C. The phosphobetaine product will have a final pH at 10% of 6–8, depending on the specific nature of the product, i.e., the nature of the amine reactant employed.

These novel phosphobetaines are good surfactants and quite unexpectedly exhibit good foam volume and superior foam stability in comparison to commercially available amphoteric and zwitterionic surfactants. This was determined by an adaptation of the well known Ross-Miles foam test principle ["Oil and Soap" 18, 99–102 (1941)] in the following manner.

Lanolin, anhydrous, cosmetic grade is mixed with dioxane (technical grade) in the proportion of 2.5 grams lanolin and 100 grams of dioxane. The lanolin is first mixed with 25 cc. of dioxane. This mixture is heated over a steam bath to 45° C. in order to dissolve the lanolin in the dioxane. The remainder of the dioxane is then added and mixed. This lanolin-dioxane solution, which is stored in an amber bottle, should be prepared fresh on the day that the tests are run.

The composition to be tested is diluted by adding 376 cc. of distilled water to 4 grams of the composition and then by adding 20 cc. of the lanolin-dioxane solution described above while mixing. Heat is produced when the lanolin-dioxane solution is added to the solution of the composition in water and care must be taken in adjusting the temperature of this solution to 24°–25° C. Both of these intermediate solutions should therefore be adjusted to 23° C. before mixing. The cooling of the lanolin-dioxane solution should be gradual in order to avoid precipitation of the lanolin. This will produce a final solution with a temperature of 24°–25° C.

The final solution of the composition to be tested, water, dioxane and lanolin described above, is then run in a modified Ross-Miles foam column in the usual way. All tests are conducted in duplicate, and the average of the two results is taken. Foam stability is determined by measuring the decay in foam height after two minutes, expressed as a percentage of the original height.

Typical foam values obtained utilizing the above procedure for an alkylamidophosphobetaine, an alkylamido betaine and an alkylamido sultaine are listed below:

| Lauric/Myristic Type | Example Number | Foam Volume (ml) | % Decay After 2 min. |
|---|---|---|---|
| Lauric Myristic Amido 3-Hydroxypropyl Phosphobetaine | 10 | 250 | 4.0 |
| Cocamido Disodium 3-Hydroxypropyl Phosphobetaine | 9 | 240 | 10 |
| Cocamido Disodium Ethyl Phosphobetaine | 48 | 210 | 19 |
| Cocamido Propylbetaine | — | 225 | 31.0 |
| Cocamido Propylsultaine | — | 200 | 60.0 |

As can be seen from the above results, the phosphobetaines of the present invention exhibit excellent foam volume and stability whereas the stability of the betaines and sultaines is significantly less.

In another series of tests, additional species of the phosphobetaine comounds of the invention were tested by a "cylinder shake test" for the evaluation of foaming characteristics.

In this test, test solutions containing 0.1% by weight of the candidate surfactant in water of 100 ppm hardness (calcium to magnesium ratio 3:2) were used and placed in 100 ml stoppered cylinders which had been cleaned so that water drains down its walls in an unbroken film. Each cylinder filled with test solution was shaken 20 times in a standard manner and net foam in ml is noted one minute and again five minutes after shaking. The tests were run in three replicates. The results were as follows:

| Lauric/Myristic Type | Example Number | 1 Minute | 5 Minutes |
|---|---|---|---|
| Lauric Myristic Amido Betaine | — | 67 | 60 |
| Sodium Lauryl Sulfate | — | 85 | 74 |
| Lauric Myristic Amido 3 Hydroxy Propyl Monosodium Phosphobetaine | 2 | 88 | 78 |
| Lauric Myristic Amido 3 Hydroxy Propyl Disodium Phosphobetaine | 10 | 85 | 78 |
| Lauric Myristic Amido 3 Hydroxy Propyl Glyceryl Phosphobetaine | 2 | 86 | 78 |
| Lauric Myristic Amido Carboxy Disodium Phosphobetaine | 62 | 87 | 73 |
| N-cocamidoethyl-N-hydroxyethyl Glycine | — | 76 | 67 |

| Coco Type | Example Number | 1 Minute | 5 Minutes |
|---|---|---|---|
| Cocobetaine | — | 65 | 56 |
| Cocamidobetaine | — | 70 | 63 |
| Cocamido Monosodium Phosphobetaine | 1 | 79 | 74 |
| Cocamido Glyceryl 3 Hydroxy Propyl Phosphobetaine | 20 | 71 | 74 |
| Coco Imidazoyl Monosodium Phosphobetaine | 37 | 83 | 78 |
| Coco Imidazoyl Disodium Phosphobetaine | 49 | 80 | 75 |
| Bis (Coco Imidazoyl) Phosphobetaine | 63 | 75 | 69 |

In addition, the compounds of the present invention possess a surprisingly low ocular irritation potential when compared to commercially available amphoteric and zwitterionic surfactants. The test employed is the modified Draize Test (J. H. Draize et al, Toilet Goods Assn. No. 17, May, 1952, No. 1 Proc. Sci. Sect.).

In this method, a 0.1 ml sample of a neutral solution of the compound under investigation is dropped into one eye of an albino rabbit, the other eye serving as a control. Six rabbits are employed for each compound.

Observations are made after 1, 24, 48, 72 and 96 hours and 7 days after initial instillation; second and third instillations are made after the 24 and 48 hour readings. Results may vary from substantially no change or only a slight irritation in the appearance of the rabbit's eye after 7 days to severe irritation and/or complete corneal opacity. Ocular lesions are scored for the cornea, iris and conjunctiva with a higher number indicating greater ocular irritation and the scores are added to give a total numerical value for each reading for 6 rabbits and average. The averaged score is an indication of the irritation potential of the composition under test. Based on the averaged score, descriptive irritation evaluation may be given, e.g., none, slight, moderate, severe, etc.

Typical results for a betaine, sultaine and a phosphobetaine in accordance with the present invention when subjected to the above test procedure are as follows:

| Compound | Eye Irritation Potential | | | | | | Irritant Rating |
|---|---|---|---|---|---|---|---|
| | 1 hr. | 24 hr. | 24 hr. | 72 hr. | 96 hr. | Day 7 | |
| Lauric Myristic Amido 3-Hydroxypropyl Phosphobetaine | 7.7 | 0.3 | 1.3 | 1.0 | 0.0 | 0.0 | slight |
| Cocamido Propylbetaine | 11.7 | 4.2 | 9.3 | 13.2 | 11.2 | 5.8 | severe |
| Cocamido Propylsultaine | 15.0 | 8.5 | 15.6 | 25.0 | — | — | severe |
| Bis Coco Imidazoline Phosphobetaine | 10.5 | 4.7 | 5.0 | 3.3 | 3.7 | 0.7 | slight |
| Cocamido Glyceryl Phosphobetaine | 9.2 | 5.0 | 4.3 | 9.0 | 5.7 | 0.7 | slight |

All tests were conducted at a concentration of 3% wt./wt.

Supportive of above test data, further series of tests were carried out as above but using only one test rabbit per compound, the following results were obtained:

| | Example Number | Day | | | | Irritant Rating |
|---|---|---|---|---|---|---|
| | | 1 | 2 | 3 | 4 | 7 | |
| Lauric Myristic Disodium Amido Phosphobetaine | 10 | 7 | 0 | 1 | 1 | 0 | very slight |

-continued

| | Example Number | Day 1 | 2 | 3 | 4 | 7 | Irritant Rating |
|---|---|---|---|---|---|---|---|
| Glyceryl "CA-35" Lauric Myristic Carboxy | 33 | 4 | 0 | 0 | 0 | 0 | very slight |
| Disodium Phosphobetaine | 62 | 2 | 2 | 0 | 0 | 0 | very slight |
| Comparison | | | | | | | |
| Amphoteric 20* | — | 21 | 15 | 7 | 5 | 0 | moderate |
| Cocobetaine | — | 23 | 26 | 19 | 17 | 25 | severe |
| Cocamidobetaine | — | 21 | 19 | 14 | 9 | 6 | severe |
| Sodium Lauryl Sulfate | — | 18 | 16 | 16 | 16 | 10 | severe |
| CA-35** | — | 26 | 21 | 21 | 16 | 0 | severe |

*N-cocamidoethyl-N-hydroxyethyl glycine
**2-undecyl-1-hydroxyethyl propionic acid imidazoline As can be readily seen, the phosphobetaines in accordance with the present invention exhibit only slight ocular irritation whereas the betaines and sultaines are severe irritants.

The preparation of specific compounds of the invention is illustrated by the following specific examples. For simplicity, there are first set forth the specific phosphate ester intermediate reactants (prepared according to reaction sequences 9–15 supra) which were used in the examples, in conjunction with certain tertiary amine reactants which are specifically set forth in each example.

Phosphate Ester Intermediate Reactants

Reactant "A"—Prepared According to Reaction Sequence 9

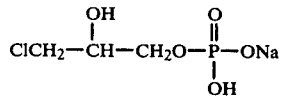

Reactant "B"—Prepared According to Reaction Sequence 10

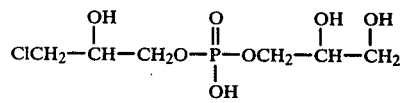

Reactant "C"—Prepared According to Reaction Sequence 11

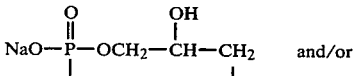

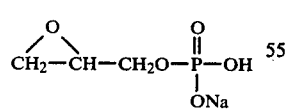

Reactant "D"—Prepared According to Reaction Sequence 12

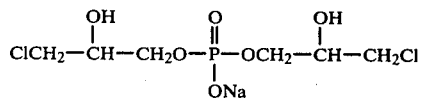

Reactant "E"—Prepared According to Reaction Sequences 13 & 14

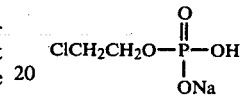

Reactant "F"

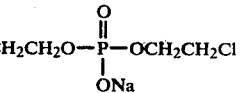

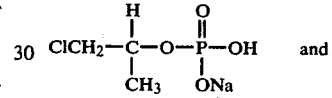

REACTANT "G"

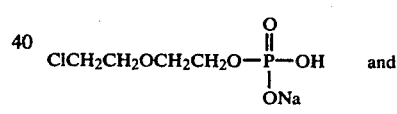

REACTANT "H"

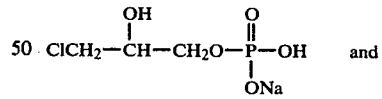

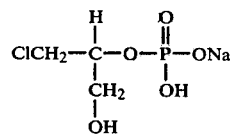

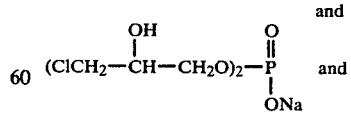

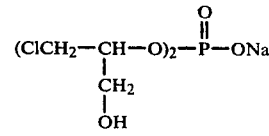

REACTANT "I"

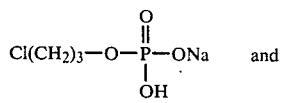

and

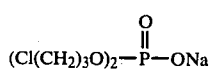

EXAMPLE 1

20.5 parts of Reactant "A" and 60.0 parts of water are charged in a reacting vessel under good agitation. Heat is applied to 50° C. 19.5 parts of molten 3-cocoamidopropyl dimethylamine are slowly charged under good agitation. Heating is continued to 90°–95° C. and held at this temperature for 3 to 4 hours. Reaction reaches 97% during this time via inorganic chloride and tertiary amine analysis.

The product is an aqueous solution of a novel product having the following structure:

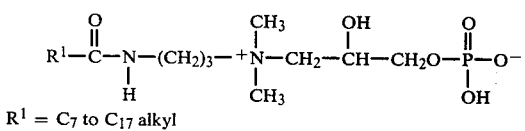

$R^1 = C_7$ to $C_{17}$ alkyl

EXAMPLE 2

20.8 parts of Reactant "A" and 60.0 parts of water are charged in a reacting vessel under good agitation. Heat is applied to approximately 50° C. 19.2 parts of a 70/30 blend of lauramidopropyl dimethylamine and myristamidopropyl dimethylamine are slowly charged to the above solution using good agitation. Heating is continued to 90°–95° C. and held at this temperature for 3 to 4 hours. Reaction reached 97% during this time via inorganic chloride and tertiary amine analysis.

The product is an aqueous solution of a novel product having the following structure:

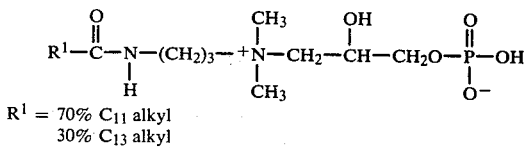

$R^1 = 70\% \ C_{11}$ alkyl
$\quad\ 30\% \ C_{13}$ alkyl

EXAMPLE 3

23.2 parts of Reactant "A" and 60.0 parts of water are charged in a reacting vessel under good agitation. Heat is applied to approximately 50° C. 16.8 parts of 3-lauramidopropyl dimethylamine are slowly charged to the above solution using good agitation. Heating is continued to 90°–95° C. and held at this temperature for 3 to 4 hours. Reaction reached 97% during this time via inorganic chloride and tertiary amine analysis.

The product is an aqueous solution of a novel product having the following structure:

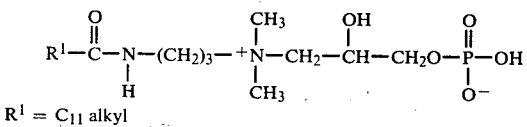

$R^1 = C_{11}$ alkyl

EXAMPLE 4

23.9 parts of Reactant "A" and 60.0 parts of water are charged in a reacting vessel under good agitation. Heat is applied to approximately 50° C. 16.1 parts of caprylamidopropyl dimethylamine are slowly charged to the above solution using good agitation. Heating is continued to 90°–95° C. and held at this temperature for 3 to 4 hours. Reaction reaches 97% during this time via inorganic chloride and tertiary amine analysis.

The product is an aqueous solution of a novel product having the following structure:

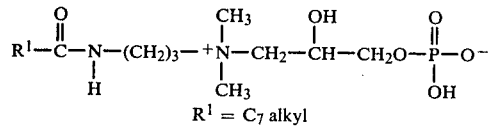

$R^1 = C_7$ alkyl

EXAMPLE 5

24.3 parts of Reactant "A" and 60.0 parts of water are charged in a reacting vessel under good agitation. Heat is applied to approximately 50° C. 15.4 parts of 3-caproamidopropyl dimethylamine are slowly charged to the above solution using good agitation. Heating is continued to 90°–05° C. and held at this temperature for 3 to 4 hours. Reaction reaches 97% during this time via inorganic chloride and tertiary amine analysis.

The product is an aqueous solution of a novel product having the following structure:

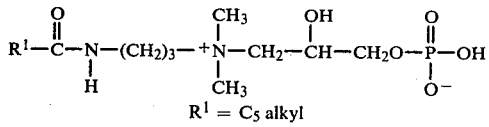

$R^1 = C_5$ alkyl

EXAMPLE 6

18.5 parts of Reactant "A" and 60.0 parts of water are charged in a reacting vessel under good agitation. Heat is applied to approximately 50° C. 21.5 parts of 3-oleamidopropyl dimethylamine are slowly charged to the above solution using good agitation. Heating is continued to 90°–95° C. and held at this temperature for 3 to 4 hours. Reaction reaches 97% during this time via inorganic chloride and tertiary amine analysis.

The product is an aqueous solution of a novel product having the following structure:

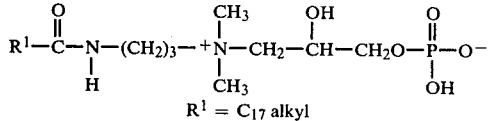

$R^1 = C_{17}$ alkyl

EXAMPLE 7

23.3 parts of Reactant "A" and 60.0 parts of water are charged in a reacting vessel under good agitation. Heat is applied to approximately 50° C. 16.7 parts of 3-cocamidopropyl diethylamine are slowly charged to the above solution using good agitation. Heating is continued to 90°–95° C. and held at this temperature for 3 to 4 hours. Reaction reaches 97% during this time via inorganic chloride and tertiary amine analysis.

The product is an aqueous solution of a novel product having the following structure:

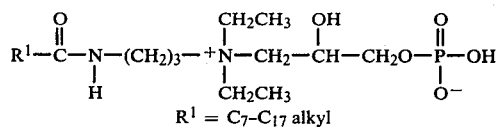

R¹ = C₇–C₁₇ alkyl

EXAMPLE 8

23.6 parts of Reactant "A" and 60.0 parts of water are charged in a reacting vessel under good agitation. Heat is applied to approximately 50° C. 16.4 parts of a blend of 70/30 3-lauramidopropyl diethylamine and 3-myristamidopropyl dimethylamine are slowly charged to the above solution using good agitation. Heating is continued to 90°–95° C. and held at this temperature for 3 to 4 hours. Reaction reaches 97% during this time via inorganic chloride and tertiary amine analysis.

The product is an aqueous solution of a novel product having the following structure:

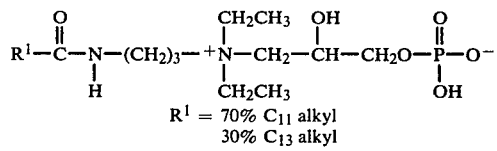

R¹ = 70% C₁₁ alkyl
30% C₁₃ alkyl

EXAMPLE 9

22.4 parts of Reactant "C" and 60.0 parts of water are charged in a reacting vessel under good agitation. Heat is applied to approximately 50° C. 17.6 parts of 3-cocamidopropyl dimethylamine are slowly charged to the above solution using good agitation. Heating is continued to 90°–95° C. and held at this temperature for 3 to 4 hours. Reaction reaches 97% during this time via inorganic chloride and tertiary amine analysis.

The product is an aqueous solution of a novel product having the following structure:

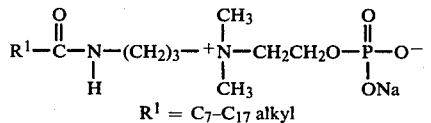

R¹ = C₇–C₁₇ alkyl

EXAMPLE 10

25.7 parts of Reactant "C" and 60.0 parts of water are charged in a reacting vessel under good agitation. Heat is applied to approximately 50° C. 14.3 parts of a blend of 70/30 lauramidopropyl dimethylamine and myristamidopropyl dimethylamine are slowly charged to the above solution using good agitation. Heating is continued to 90°–95° C. and held at this temperature for 3 to 4 hours. Reaction reaches 97% during this time via inorganic chloride and tertiary amine analysis.

The product is an aqueous solution of a novel product having the following structure:

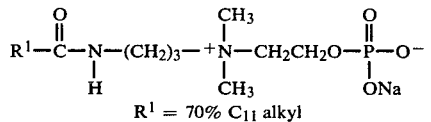

R¹ = 70% C₁₁ alkyl
30% C₁₃ alkyl

EXAMPLE 11

20.8 parts of Reactant "C" and 60.0 parts of water are charged in a reacting vessel under good agitation. Heat is applied to approximately 50° C. 19.2 parts of a 70/30 blend of 3-lauramidopropyl dimethylamine and 3-myristamidopropyl dimethylamine are slowly charged to the above solution using good agitation. Heating is continued to 90°–95° C. and held at this temperature for 3 to 4 hours. Reaction reaches 97% during this time via inorganic chloride and tertiary amine analysis.

The product is an aqueous solution of a novel product having the following structure:

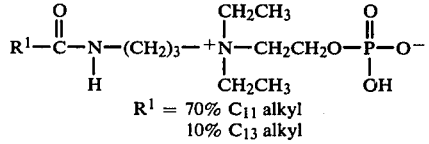

R¹ = 70% C₁₁ alkyl
10% C₁₃ alkyl

EXAMPLE 12

23 parts of Reactant "B" and 60.0 parts of water are charged in a reacting vessel under good agitation. Heat is applied to approximately 50° C. 17 parts of molten 3-cocamidopropyl dimethylamine are slowly charged under good agitation. Heating is continued to 90°–95° C. and held at this temperature for 3 to 4 hours. Reaction reaches 98% during this time via inorganic chloride and tertiary amine analysis.

The product is an aqueous solution of a novel product having the following structure:

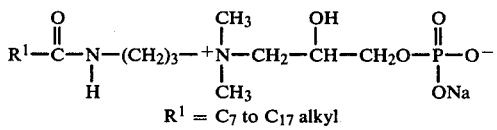

R¹ = C₇ to C₁₇ alkyl

EXAMPLE 13

23.4 parts of Reactant "B" and 60.0 parts of water are charged in a reacting vessel under good agitation. Heat is applied to approximately 50° C. 16.6 parts of a 70/30 blend of 3-lauramidopropyl dimethylamine and 3-myristamidopropyl dimethylamine are slowly charged to the above solution using good agitation. Heating is continued to 90°–95° C. and held at this temperature for 3 to 4 hours. Reaction reaches 98% during this time via inorganic chloride and tertiary amine analysis.

The product is an aqueous solution of a novel product having the following structure:

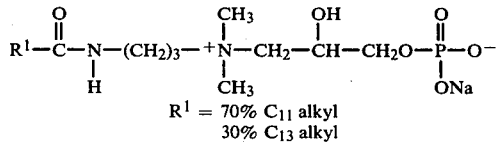

R¹ = 70% C₁₁ alkyl
30% C₁₃ alkyl

EXAMPLE 14

25.7 parts of Reactant "B" and 60.0 parts of water are charged in a reacting vessel under good agitation. Heat is applied to approximately 50° C. 14.3 parts of 3-lauramidopropyl dimethylamine are slowly charged to the above solution using good agitation. Heating is continued to 90°–95° C. and held at this temperature for 3 to 4 hours. Reaction reaches 98% during this time via inorganic chloride and tertiary amine analysis.

The product is an aqueous solution of a novel product having the following structure:

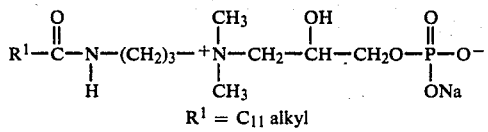

R¹ = C₁₁ alkyl

EXAMPLE 15

26.4 parts of Reactant "B" and 60.0 parts of water are charged in a reacting vessel under good agitation. Heat is applied to approximately 50° C. 13.6 parts of 3-caprylamidopropyl dimethylamine are slowly charged to the above solution using good agitation. Heating is continued to 90°–95° C. and held at this temperature for 3 to 4 hours. Reaction reaches 98% during this time via inorganic chloride and tertiary amine analysis.

The product is an aqueous solution of a novel product having the following structure:

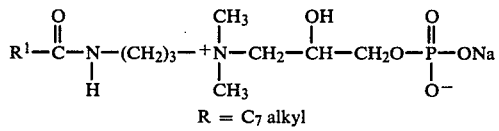

R = C₇ alkyl

EXAMPLE 16

26.8 part of Reactant "B" and 60.0 parts of water are charged in a reacting vessel under good agitation. Heat is applied to approximately 50° C. 13.2 parts of 3-caproamidopropyl dimethylamine are slowly charged to the above solution using good agitation. Heating is continued to 90°–95° C. and the heated mixture held at this temperature for 3 to 4 hours. Reaction reaches 98% during this time via inorganic chloride and tertiary amine analysis.

The product is an aqueous solution of a novel product having the following structure:

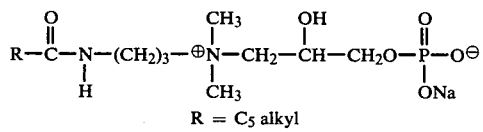

R = C₅ alkyl

EXAMPLE 17

21.0 parts of Reactant "B" and 60.0 parts of water are charged in a reacting vessel under good agitation. Heat is applied to approximately 50° C. 19.0 parts of 3-oleamidopropyl dimethylamine are slowly charged to the above solution using good agitation. Heating is continued to 90°–95° C. and the heated mixture held at this temperature for 3 to 4 hours. Reaction reaches 98% during this time via inorganic chloride and tertiary amine analysis.

The product is an aqueous solution of a novel product having the following structure:

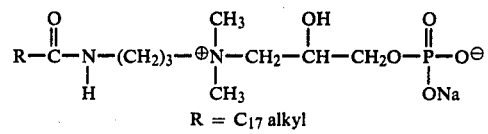

R = C₁₇ alkyl

EXAMPLE 18

25.8 parts of Reactant "B" and 60.0 parts of water are charged in a reacting vessel under good agitation. Heat is applied to approximately 50° C. 14.2 parts of 3-cocamidopropyl diethylamine are slowly charged to the above solution using good agitation. Heating is continued to 90°–95° C. and the heated mixture held at this temperature for 3 to 4 hours. Reaction reaches 98% during this time via inorganic chloride and tertiary amine analysis.

The product is an aqueous solution of a novel product having the following structure:

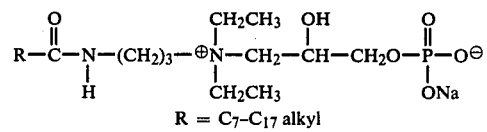

R = C₇–C₁₇ alkyl

EXAMPLE 19

26.2 parts of Reactant "B" and 60.0 parts of water are charged in a reacting vessel under good agitation. Heat is applied to approximately 50° C. 13.8 parts of a 70/30 blend of 3-lauramidopropyl diethylamine and 3-myristamidopropyl diethylamine are slowly charged to the above solution using good agitation. Heating is continued to 90°–95° C. and the heated mixture held at this temperature for 3 to 4 hours. Reaction reaches 98% during this time via inorganic chloride and tertiary amine analysis.

The product is an aqueous solution of a novel product having the following structure:

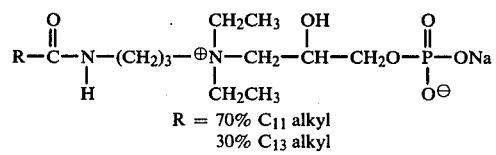

R = 70% C₁₁ alkyl
30% C₁₃ alkyl

EXAMPLE 20

20.4 parts of Reactant "D" and 60.0 parts of water are charged in a reacting vessel under good agitation. Heat is applied to 50° C. 19.6 parts of molten 3-cocamidopropyl dimethylamine are slowly charged under good agitation. Heating is continued to 90°–95° C. and the heated mixture held at this temperature for 3 to 4 hours. Reaction reaches 98% during this time via inorganic chloride and tertiary amine analysis.

The product is an aqueous solution of a novel product having the following structure:

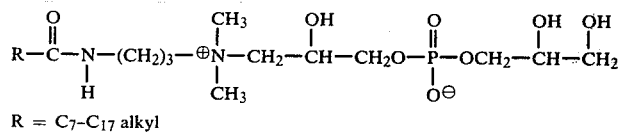

R = C₇–C₁₇ alkyl

EXAMPLE 21

20.8 parts of Reactant "D" and 60.0 parts of water are charged in a reacting vessel under good agitation. Heat is applied to approximately 50° C. 19.2 parts of a 70/30 blend of 3-lauramidopropyl dimethylamine and 3-myristamidopropyl dimethylamine are slowly charged to the above solution using good agitation. Heating is continued to 90°–95° C. and the heated mixture held at this temperature for 3 to 4 hours. Reaction reaches 98% during this time via inorganic chloride and tertiary amine analysis.

The product is an aqueous solution of a novel product having the following structure:

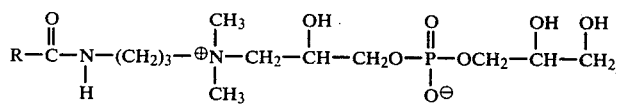

R = 70% C₁₁ alkyl
    30% C₁₃ alkyl

EXAMPLE 22

23.1 parts of Reactant "D" and 60.0 parts of water are charged in a reacting vessel under good agitation. Heat is applied to approximately 50° C. 16.9 parts of 3-lauramidopropyl dimethylamine are slowly charged to the above solution using good agitation. Heating is continued to 90°–95° C. and the heated mixture held at this temperature for 3 to 4 hours. Reaction reaches 98% during this time via inorganic chloride and tertiary amine analysis.

The product is an aqueous solution of a novel product having the following structure.

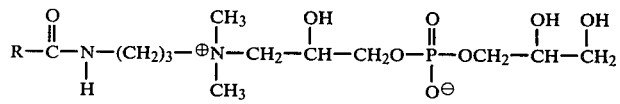

R = C₁₁ alkyl

EXAMPLE 23

23.2 parts of Reactant "D" and 60.0 parts of water are charged in a reacting vessel under good agitation. Heat is applied to approximately 50° C. 16.2 parts of 3-caprylamidopropyl dimethylamine are slowly charged to the above solution using good agitation. Heating is continued to 90°–95° C. and the heated mixture held at this temperature for 3 to 4 hours. Reaction reaches 98% during this time via inorganic chloride and tertiary amine analysis.

The product is an aqueous solution of a novel product having the following structure:

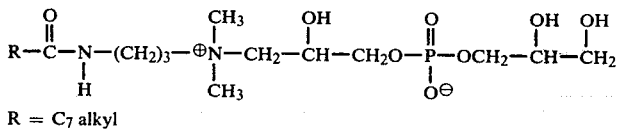

R = C₇ alkyl

EXAMPLE 24

24.3 parts of Reactant "D" and 60.0 parts of water are charged in a reacting vessel under good agitation. Heat is applied to approximately 50° C. 15.7 parts of 3-caproamidopropyl dimethylamine are slowly charged to the above solution using good agitation. Heating is continued to 90°–95° C. and the heated mixture held at this temperature for 3 to 4 hours. Reaction reaches 98% during this time via inorganic chloride and tertiary amine analysis.

The product is an aqueous solution of a novel product having the following structure:

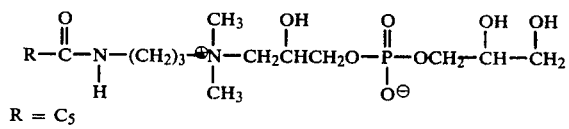

R = C₅

EXAMPLE 25

21.6 parts of Reactant "D" and 60.0 parts of water are charged in a reacting vessel under good agitation. Heat is applied to approximately 50° C. 18.4 parts of 3-oleamidopropyl dimethylamine are slowly charged to the above solution using good agitation. Heating is continued to 90°–95° C. and the heated mixture held at this temperature for 3 to 4 hours. Reaction reaches 98% during this time via inorganic chloride and tertiary amine analysis.

The product is an aqueous solution of a novel product having the following structure:

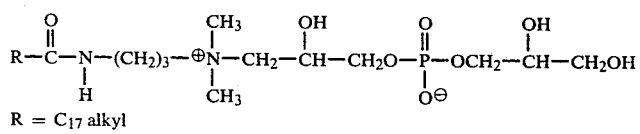

R = C₁₇ alkyl

EXAMPLE 26

26.8 parts of Reactant "D" and 60.0 parts of water are charged in a reacting vessel under good agitation. Heat is applied to approximately 50° C. 13.2 parts of 3-cocamidopropyl dimethylamine are slowly charged to the above solution using good agitation. Heating is continued to 90°–95° C. and the heated mixture held at this temperature for 3 to 4 hours. Reaction reaches 98% during this time via inorganic chloride and tertiary amine analysis.

The product is an aqueous solution of a novel product having the following structure:

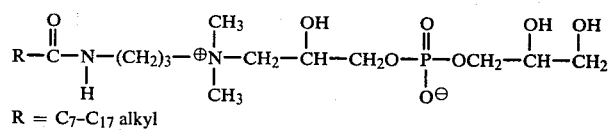

R = C₇–C₁₇ alkyl

EXAMPLE 27

26.4 parts of Reactant "D" and 60.0 parts of water are charged in a reacting vessel under good agitation. Heat is applied to approximately 50° C. 13.6 parts of a 70/30 blend of 3-lauramidopropyl diethylamine and 3-myristamidopropyl diethylamine are slowly charged to the above solution using good agitation. Heating is continued to 90°–95° C. and the heated mixture held at this temperature for 3 to 4 hours. Reaction reaches 98% during this time via inorganic chloride and tertiary amine analysis.

The product is an aqueous solution of a novel product having the following structure:

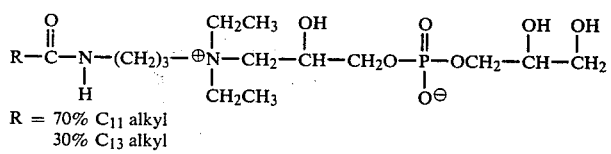

R = 70% C₁₁ alkyl
30% C₁₃ alkyl

EXAMPLE 28

14.4 parts of Reactant "E" and 60.0 parts of water are charged in a reacting vessel under good agitation. Heat is applied to 50° C. 25.6 parts of molten 3-cocamidopropyl dimethylamine are slowly charged under good agitation. Heating is continued to 90°–95° C. and the heated mixture held at this temperature for 3 to 4 hours. Reaction reaches 98% during this time via inorganic chloride and tertiary amine analysis.

The product is an aqueous solution of a novel product having the following structure:

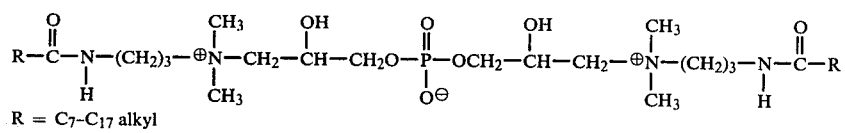

R = C₇–C₁₇ alkyl

EXAMPLE 29

15.3 parts of Reactant "E" and 60.0 parts of water are charged in a reacting vessel under good agitation. Heat is applied to approximately 50° C. 24.7 parts of 70/30 blend of 3-lauramidopropyl dimethylamine and 3-myristamidopropyl dimethylamine are slowly charged to the above solution using good agitation. Heating is continued to 90°–95° C. and the heated mixture held at this temperature for 3 to 4 hours. Reaction reaches 98% during this time via inorganic chloride and tertiary amine analysis.

The product is an aqueous solution of a novel product having the following structure:

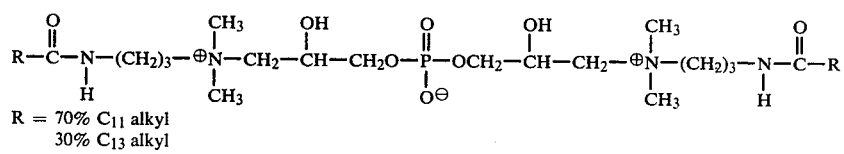

R = 70% C₁₁ alkyl
30% C₁₃ alkyl

EXAMPLE 30

20.7 parts of Reactant "E" and 60.0 parts of water are charged in a reacting vessel under good agitation. Heat is applied to approximately 50° C. 19.3 parts of 3-caprylamidopropyl dimethylamine are slowly charged to the above solution using good agitation. Heating is continued to 90°–95° C. and the heated mixture held at this temperature for 3 to 4 hours. Reaction reaches 98% during this time via inorganic chloride and tertiary amine analysis.

The product is an aqueous solution of a novel product having the following structure:

$$R-\overset{O}{\underset{H}{\overset{\|}{C}}}-\overset{}{\underset{}{N}}-(CH_2)_3-\overset{CH_3}{\underset{CH_3}{\overset{\oplus}{N}}}-CH_2-\overset{OH}{\underset{}{CH}}-CH_2O-\overset{O}{\underset{O^{\ominus}}{\overset{\|}{P}}}-OCH_2-\overset{OH}{\underset{}{CH}}-CH_2-\overset{CH_3}{\underset{CH_3}{\overset{\oplus}{N}}}-(CH_2)_3-\overset{}{\underset{H}{N}}-\overset{O}{\overset{\|}{C}}-R$$

R = C₇ alkyl

EXAMPLE 31

30.3 parts of Reactant "E" and 60.0 parts of water are charged in a reacting vessel under good agitation. Heat is applied to approximately 50° C. 9.7 parts of 3-caproamidopropyl dimethylamine are slowly charged to the above solution using good agitation. Heating is continued to 90°–95° C. and the heated mixture held at this temperature for 3 to 4 hours. Reaction reaches 98% during this time via inorganic chloride and tertiary amine analysis.

The product is an aqueous solution of a novel product having the following structure:

$$R-\overset{O}{\overset{\|}{C}}-\underset{H}{N}-(CH_2)_3-\overset{CH_3}{\underset{CH_3}{\overset{\oplus}{N}}}-CH_2-\overset{OH}{CH}-CH_2O-\overset{O}{\underset{O^{\ominus}}{\overset{\|}{P}}}-CH_2-\overset{OH}{CH}-CH_2-\overset{CH_3}{\underset{CH_3}{N}}-(CH_2)_3-\underset{H}{N}-\overset{O}{\overset{\|}{C}}-R$$

R = C₅ alkyl

EXAMPLE 32

16.0 parts of Reactant "E" and 60.0 parts of water are charged in a reacting vessel under good agitation. Heat is applied to approximately 50° C. 24.0 parts of 3-oleamidopropyl dimethylamine are slowly charged to the above solution using good agitation. Heating is continued to 90°–95° C. and the heated mixture held at this temperature for 3 to 4 hours. Reaction reaches 98% during this time via inorganic chloride and tertiary amine analysis.

The product is an aqueous solution of a novel product having the following structure:

$$R-\overset{O}{\overset{\|}{C}}-\underset{H}{N}-(CH_2)_3-\overset{CH_3}{\underset{CH_3}{\overset{\oplus}{N}}}-CH_2-\overset{OH}{CH}-CH_2O-\overset{O}{\underset{O^{\ominus}}{\overset{\|}{P}}}-OCH_2-\overset{OH}{CH}-CH_2-\overset{CH_3}{\underset{CH_3}{N}}-(CH_2)_3-\underset{H}{N}-\overset{O}{\overset{\|}{C}}-R$$

R = C₁₇ alkyl

EXAMPLE 33

20.70 parts of Reactant "B" and 60.0 parts of soft water are charged into a suitable reactor under good agitation. Heat is applied to 50° C. 19.30 parts of 2-undecyl-1-hydroxyethyl propionic acid imidazoline are charged under good agitation and heating is continued to 90°–95° C. and the heated mixture held at this temperature for 4 hours. The reaction is complete when inorganic chloride reaches 97% of theoretical.

The product is an aqueous solution of a novel product having the following structure:

[Structure with imidazoline ring]
$$\text{N-CH}_2\text{CHCH}_2\text{O-P-O-CH}_2\text{CHCH}_2\text{OH}$$ with OH groups, O⁻ on P, and CH₂CH₂OCH₂CH₂—C(=O)—ONa substituent

R = C₁₁

EXAMPLE 34

29.7 parts of Reactant "E" and 60.0 parts of water are charged in a reacting vessel under good agitation. Heat is applied to approximately 50° C. 12.1 parts of 3-caproamidopropyl diethylamine are slowly charged to the above solution using good agitation. Heating is continued to 90°–95° C. and the heated mixture held at this temperature for 3 to 4 hours. Reaction reaches 98% during this time via inorganic chloride and tertiary amine analysis.

The product is an aqueous solution of a novel product having the following structure:

$$R-\overset{O}{\overset{\|}{C}}-\underset{H}{N}-(CH_2)_3-\overset{CH_2CH_3}{\underset{CH_2CH_3}{\overset{\oplus}{N}}}-CH_2-\overset{OH}{CH}-CH_2O-\overset{O}{\underset{O^{\ominus}}{\overset{\|}{P}}}-OCH_2\overset{OH}{CH}CH_2-\overset{CH_2CH_3}{\underset{CH_2CH_3}{\overset{\oplus}{N}}}-(CH_2)_3-\underset{H}{N}-\overset{O}{\overset{\|}{C}}-R$$

R = C₇ alkyl

EXAMPLE 35

21.7 parts of Reactant "C" and 60.0 parts of water are charged into a reacting vessel under good agitation. Heat is applied to approximately 50° C. 18.3 parts of a 70/30 blend of lauramido ethyl 2,6-dimethyl morphline and myristamido ethyl 2,6-dimethyl morphline are slowly charged to the above solution using good agitation. Heating is continued to 90°–95° C. and the heated mixture held at this temperature for 3 to 4 hours. Reaction reaches 98% during this time via inorganic chloride and tertiary amine analysis.

The product is an aqueous solution of a novel product having the following structure

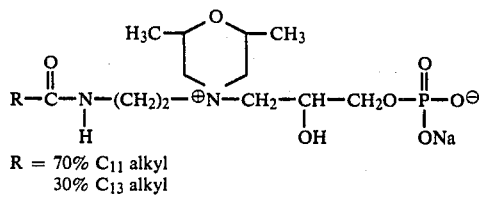

R = 70% C₁₁ alkyl
30% C₁₃ alkyl

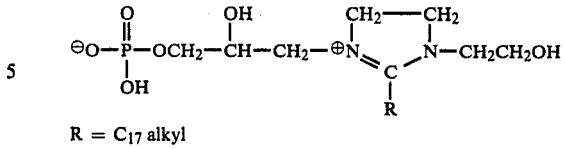

R = C₁₇ alkyl

EXAMPLE 36

26.7 parts of Reactant "C" and 60.0 parts of water are charged into a reacting vessel under good agitation. Heat is applied to approximately 50° C. 13.3 parts of 3-benzamido propyl dimethylamine are slowly charged to the above solution using good agitation. Heating is continued to 90°–95° C. and the heated mixture held at this temperature for 3 to 4 hours. Reaction reaches 98% during this time via inorganic chloride and tertiary amine analysis.

The product is an aqueous solution of a novel product having the following structure:

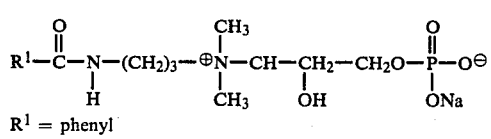

R¹ = phenyl

EXAMPLE 37

22.88 parts of Reactant "A" and 60.0 parts water are charged into a suitable reaction vessel under good agitation. Heat is applied to 50° C. 17.12 parts of 1-hydroxyethyl-2-alkyl-2-imidazoline (the alkyl has 7+17 carbon atoms) are charged under good agitation. Heating is continued to 90°–95° C. and the heated mixture held at this temperature for 4 hours. Reaction reaches 97% during this time via inorganic chloride and tertiary amine analysis.

The product is an aqueous solution of a novel product having the following structure:

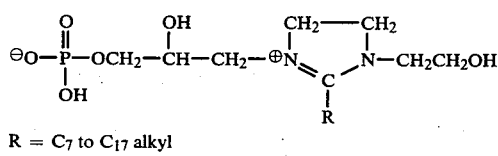

R = C₇ to C₁₇ alkyl

EXAMPLE 38

20.8 parts of Reactant "A" and 60.0 parts of water are charged into a suitable reaction vessel under good agitation. Heat is applied to 50° C. 19.2 parts of 1-hydroxyethyl 2-alkyl-2-imidazoline (being C₁₇) are charged under good agitation. Heating is continued to 90°–95° C. and the heated mixture held at this temperature for 4 hours. Reaction reaches 97% during this time via inorganic chloride and tertiary amine analysis.

The product is an aqueous solution of a novel product having the following structure:

EXAMPLE 39

21.45 parts of Reactant "A" and 60.0 parts water are charged into a suitable reaction vessel under good agitation. Heat is applied to 50° C. 18.55 parts of 1-hydroxyethyl-2-alkyl-2-imidazoline (being 70% C₁₁ and 30% C₁₃) are charged under good agitation. Heating is continued to 90°–95° C. and the heated mixture held at this temperature for 4 hours. Reaction reaches 97% during this time via inorganic chloride and tertiary amine analysis.

The product is an aqueous solution of a novel product having the following structure:

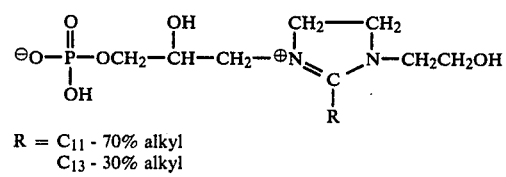

R = C₁₁ - 70% alkyl
C₁₃ - 30% alkyl

EXAMPLE 40

23.32 parts of Reactant "A" and 60.0 parts water are charged into a suitable reaction vessel under good agitation. Heat is applied to 50° C. 16.68 parts of 1-hydroxyethyl-2-alkyl-2-imidazoline (being C₁₁) are charged under good agitation. Heating is continued to 90°–95° C. and the heated mixture held at this temperature for 4 hours. Reaction reaches 97% during this time via inorganic chloride and tertiary amine analysis.

The product is an aqueous solution of a novel product having the following structure:

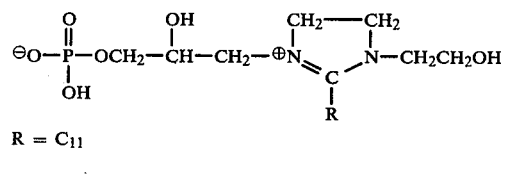

R = C₁₁

EXAMPLE 41

26.0 parts of Reactant "A" and 60.0 parts water are charged into a suitable reaction vessel under good agitation. Heat is applied to 50° C. 14.0 parts of 1-hydroxyethyl-2-alkyl-2-imidazoline (being C₇) are charged under good agitation. Heating is continued to 90°–95° C. and the heated mixture held at this temperature for 4 hours. Reaction reaches 97% during this time via inorganic chloride and tertiary amine analysis.

The product is an aqueous solution of a novel product having the following structure:

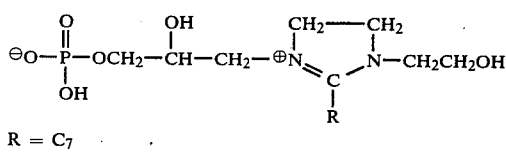

R = C₇

EXAMPLE 42

27.56 parts of Reactant "A" and 60.0 parts water are charged into a suitable reaction vessel under good agitation. Heat is applied to 50° C. 12.44 parts of 1-hydroxyethyl-2-alkyl-2-imidazoline (being C₅) are charged under good agitation. Heating is continued to 90°–95° C. and the heated mixture held at this temperature for 4 hours. Reaction reaches 97% during this time via inorganic chloride and tertiary amine analysis.

The product is an aqueous solution of a novel product having the following structure:

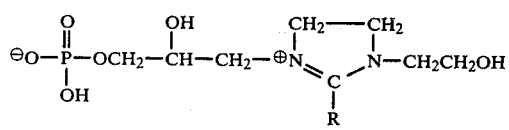

R = C₅ alkyl

EXAMPLE 43

19.72 parts of Reactant "F" and 60.0 parts of water are charged into a suitable reaction vessel under good agitation. Heat is applied to 50° C. 20.28 parts of 3-cocamidopropyl dimethylamine are charged under good agitation. Heating is continued to 90°–95° C. and the heated mixture held at this temperature for 4 hours. Reaction is complete when inorganic chloride reaches theoretical and residual 3°N is vanishingly small.

The produce is an aqueous solution of a novel product having the following structure:

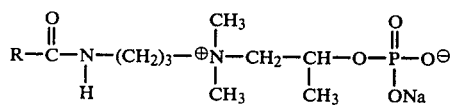

and

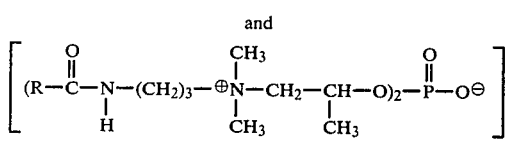

R = C₇ to C₁₇ alkyl

EXAMPLE 44

20.69 parts of Reactant "F" and 60.0 parts of water are charged into a suitable reaction vessel under good agitation. Heat is applied to 50° C. 19.31 parts of 1-hydroxyethyl-2-alkyl-2-imidazoline* are charged under good agitation. Heating is continued to 90°–95° C. and the heated mixture held at this temperature for 4 hours. Reaction is complete when inorganic chloride reaches theoretical and residual 3°N is vanishingly small.
*(alkyl being C₇ to C₁₇)

The product is an aqueous solution of a novel product having the following structure:

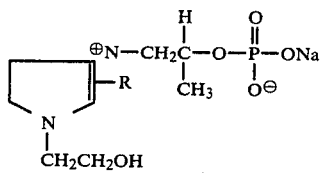

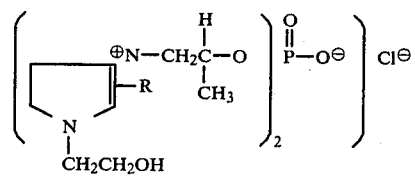

R = C₇ to C₁₇ alkyl

EXAMPLE 45

20.72 parts of Reactant "G" and 60.0 parts of water are charged into a suitable reaction vessel under good agitation. Heat is applied to 50° C. 19.28 parts of 3-cocamidopropyl dimethylamine are charged under good agitation. Heating is continued to 90°–95° C. and the heated mixture held at this temperature for 4 hours. Reaction is complete when inorganic chloride reaches theoretical and residual 3°N is vanishingly small.

The product is an aqueous solution of a novel product having the following structure:

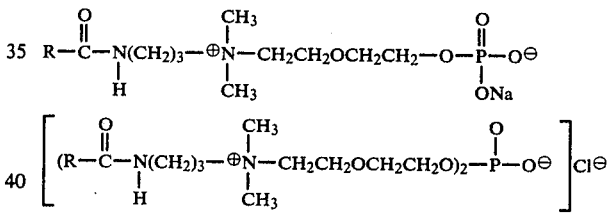

R = C₇ to C₁₇

EXAMPLE 46

21.70 parts of Reactant "G" and 60.0 parts of water are charged into a suitable reaction vessel under good agitation. Heat is applied to 50° C. 18.30 parts of 1-hydroxyethyl 2-alkyl-2-imidazoline* are charged under good agitation. Heating is continued to 90°–95° C. and the heated mixture is held at this temperature for 4 hours. Reaction is complete when inorganic chloride reaches theoretical and residual 3°N is vanishingly small.
*(alkyl being C₇ to C₁₇)

The product is an aqueous solution of a novel product having the following structure:

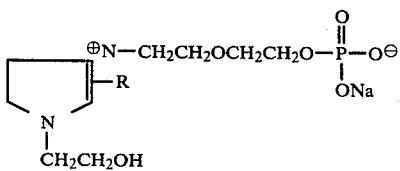

and

-continued

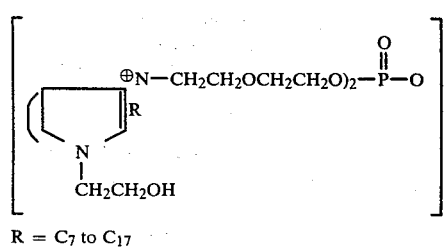

R = C₇ to C₁₇

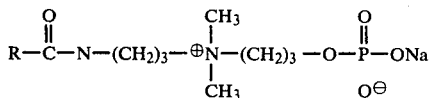

and

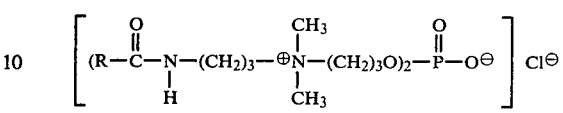

R = C₇ to C₁₇ alkyl

EXAMPLE 47

20.30 parts of Reactant "H" and 60.0 parts of water are charged into a suitable reaction vessel under good agitation. Heat is applied to 50° C. 19.70 parts of 3-cocamidopropyl dimethyamine are charged under good agitation. Heating is continued to 90°–95° C. and the heated mixture held at this temperature for 4 hours. Reaction is complete when inorganic chloride reaches theoretical and residual 3°N is vanishingly small.

The product is an aqueous solution of a novel product having the following structure:

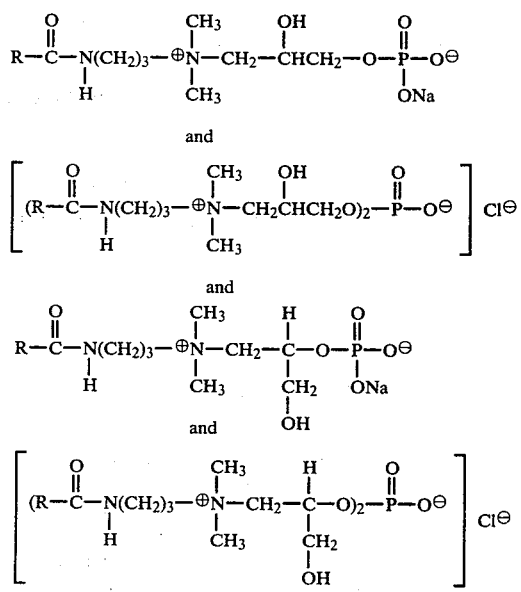

R = C₇ to C₁₇ alkyl

EXAMPLE 48

20.90 parts of Reactant "I" and 60.0 parts of water are charged into a suitable reaction vessel under good agitation. Heat is applied to 50° C. 19.10 parts of 3-cocamidopropyl dimethamine are charged under good agitation. Heating is continued to 90°–95° C. and the heated mixture held at this temperature for 4 hours. Reaction is complete when inorganic chloride reaches theoretica and residual 3°N is vanishingly small.

The product is an aqueous solution of a novel product having the following structure:

EXAMPLE 49

23.9 parts of Reactant "C" and 60.0 parts water are charged into a suitable reaction vessel under good agitation. Heat is applied to 50° C. 16.1 parts of 1-hydroxyethyl-2-alkyl-2-imidazoline (alkyl having 7–17 carbons) are charged under good agitation. Heating is continued to 90°–95° C. and the heated mixture is held at this temperature for 4 hours. Reaction reaches 97% during this time via inorganic chloride and tertiary amine analysis.

The product is an aqueous solution of a novel product having the following structure:

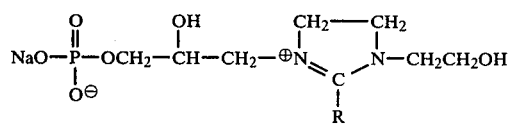

R = C₇ to C₁₇ alkyl

EXAMPLE 50

20.2 parts of Reactant "C" and 60.0 parts water are charged into a suitable reaction vessel under good agitation. Heat is applied to 50° C. 19.8 parts of 1 hydroxyethyl-2-alkyl-2-imidazoline (being C₁₇) are charged under good agitation. Heating is continued to 90°–95° C. and the heated mixture held at this temperature for 4 hours. Reaction reaches 97% during this time via inorganic chloride and tertiary amine analysis The product is an aqueous solution of a novel product having the following structure:

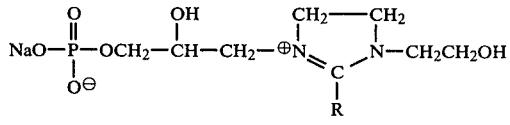

R = C₁₇ alkyl

EXAMPLE 51

22.4 parts of Reactant "C" and 60.0 parts water are charged into a suitable reaction vessel under good agitation. Heat is applied to 50° C. 17.6 parts of 1-hydroxyethyl-2-alkyl-2-imidazoline (being C₁₁) are charged under good agitation. Heating is continued to 90°–95° C., and the heated mixture held at this temperature for 4 hours. Reaction reaches 97% during this time via inorganic chloride and tertiary amine analysis.

The product is an aqueous solution of a novel product having the following structure:

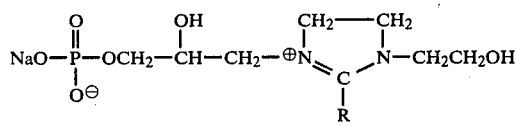

R = C₁₁ 70% alkyl
C₁₃ 30% alkyl

EXAMPLE 52

24.3 parts of Reactant "C" and 60.0 parts water are charged into a suitable reaction vessel under good agitation. Heat is applied to 50° C. 15.7 parts of 1-hydroxyethyl-2-alkyl-2-imidazoline (being C₁₁) are charged under good agitation. Heating is continued to 90°-95° C. and the heated mixture held at this temperature for 4 hours. Reaction reaches 97% during this time via inorganic chloride and tertiary amine analysis.

The produce is an aqueous solution of a novel product having the following structure:

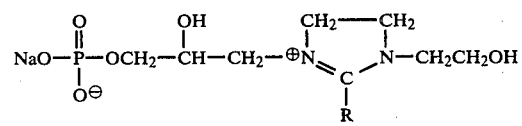

R = C₁₁ alkyl

EXAMPLE 53

26.9 parts of Reactant "C" and 60.0 parts water are charged into a suitable reaction vessel under good agitation. Heat is applied to 50° C. 13.1 parts of 1-hydroxyethyl-2-alkyl-2-imidazoline (being C₇) are charged under good agitation. Heating is continued to 90°-95° C. and the heated mixture held at this temperature for 4 hours. Reaction reaches 97% during this time via inorganic chloride and tertiary amine analysis.

The product is an aqueous solution of a novel product having the following structure:

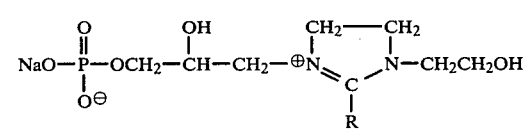

R = C₇ alkyl

EXAMPLE 54

28.4 parts of Reactant "C" and 60.0 parts water are charged into a suitable reaction vessel under good agitation. Heat is applied to 50° C. 11.6 parts of 1-hydroxyethyl-2-alkyl-2-imidazoline (being C₅) are charged under good agitation. Heating is continued to 90°-95° C. and the heated mixture held at this temperature for 4 hours. Reaction reaches 97% during this time via inorganic chloride and teritary amine analysis.

The product is an aqueous solution of a novel product having the following structure:

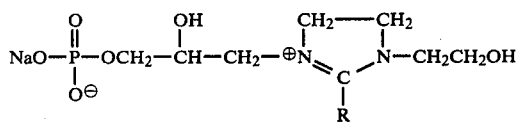

R = C₅ alkyl

EXAMPLE 55

25.0 parts of Reactant "B" and 60.0 parts water are charged into a suitable reaction vessel under good agitation. Heat is applied to 50° C. 15.0 parts of 1-hydroxyethyl-2-alkyl-2-imidazoline (alkyl having 7-17 carbons) are charged under good agitation. Heating is continued to 90°-95° C. and the heated mixture held at this temperature for 4 hours. Reaction reaches 97% during this time via inorganic chloride and tertiary amine analysis.

The product is an aqueous solution of a novel product having the following structure:

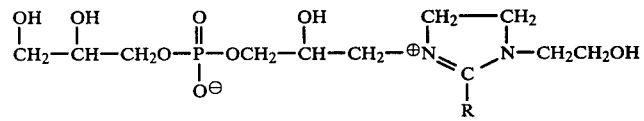

R = C₇ to C₁₇ alkyl

EXAMPLE 56

21.4 parts of Reactant "B" and 60.0 parts water are charged into a suitable reaction vessel under good agitation. Heat is applied to 50° C. 18.6 parts of 1-hydroxyethyl-2-alkyl-2-imidazoline (being C₁₇) are charged under good agitation. Heating is continued to 90°-95° C., and the heated mixture held at this temperature for 4 hours. Reaction reaches 97% during this time via inorganic chloride and tertiary amine analysis.

The product is an aqueous solution of a novel product having the following structure:

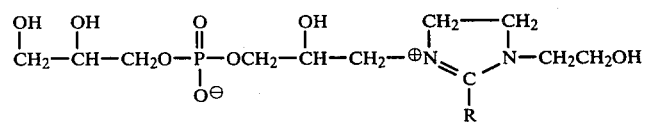

R = C₁₇ alkyl

EXAMPLE 57

23.6 parts of Reactant "B" and 60.0 parts water are charged into a suitable reaction vessel under good agitation. Heat is applied to 50° C. 16.4 parts of 1-hydroxyethyl-2-alkyl-2-imidazoline (being 70% $C_{11}$ and 30% $C_{13}$) are charged under good agitation. Heating is continued to 90°–95° C. and the heated mixture held at this temperature for 4 hours. Reaction reaches 97% during this time via inorganic chloride and tertiary amine analysis.

The product is an aqueous solution of a novel product having the following structure:

$$CH_2-CH-CH_2O-P(=O)(O^{\ominus})-OCH_2-CH(OH)-CH_2-{}^{\oplus}N\cdots C(R)\cdots N-CH_2CH_2OH$$
(with $OH$, $OH$ on first two carbons; imidazoline ring $CH_2-CH_2$)

R = $C_{11}$ - 70% alkyl
    $C_{13}$ - 30% alkyl

EXAMPLE 58

25.4 parts of Reactant "B" and 60.0 parts water are charged into a suitable reaction vessel under good agitation. Heat is applied to 50° C. 14.6 parts of 1-hydroxyethyl-2-alkyl-2-imidazoline (being $C_{11}$) are charged under good agitation. Heating is continued to 90°–95° C. and the heated mixture held at this temperature for 4 hours. Reaction reaches 97% during this time via inorganic chloride and tertiary amine analysis.

The product is an aqueous solution of a novel product having the following structure:

$$CH_2(OH)-CH(OH)-CH_2O-P(=O)(O^{\ominus})-OCH_2-CH(OH)-CH_2-{}^{\oplus}N\cdots C(R)\cdots N-CH_2CH_2OH$$

R = $C_{11}$ alkyl

EXAMPLE 59

27.9 parts of Reactant "B" and 60.0 parts water are charged into a suitable reaction vessel under good agitation. Heat is applied to 50° C. 12.1 parts of 1-hydroxyethyl-2-alkyl-2-imidazoline (being $C_7$) are charged under good agitation. Heating is continued for 4 hours. Reaction reaches 97% during this time via inorganic chloride and tertiary amine analysis.

The product is an aqueous solution of a novel product having the following structure:

$$CH_2(OH)-CH(OH)-CH_2O-P(=O)(O^{\ominus})-OCH_2-CH(OH)-CH_2-{}^{\oplus}N\cdots C(R)\cdots N-CH_2CH_2OH$$

R = $C_7$ alkyl

EXAMPLE 60

29.4 parts of Reactant "B" and 60.0 parts water are charged into a suitable reaction vessel under good agitation. Heat is applied to 50° C. 10.6 parts of 1-hydroxyethyl-2-alkyl-2-imidazoline (being $C_5$) are charged under good agitation. Heating is continued for 4 hours. Reaction reaches 97% during this time via inorganic chloride and tertiary amine analysis.

The product is an aqueous solution of a novel product having the following structure:

$$CH_2(OH)-CH(OH)-CH_2O-P(=O)(O^{\ominus})-OCH_2-CH(OH)-CH_2-{}^{\oplus}N\cdots C(R)\cdots N-CH_2CH_2OH$$

R = $C_5$ alkyl

EXAMPLE 61

25.8 parts of Reactant "B" and 60.0 parts water are charged into a suitable reaction vessel under good agitation. Heat is applied to 50° C. 14.2 parts of alkyldimethylamine (alkyl being $C_{12}$) are charged under good agitation. Heating is continued to 90°–95° C. and the heated mixture held at this temperature for 4 hours. Reaction reaches 97% during this time via inorganic chloride and tertiary amine analysis.

The produce is an aqueous solution of a novel product having the following structure:

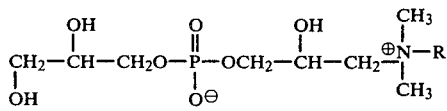

R = $C_{12}$ during this time via inorganic chloride and tertiary amine analysis.

The product is an aqueous solution of one of the novel products having the following structure:

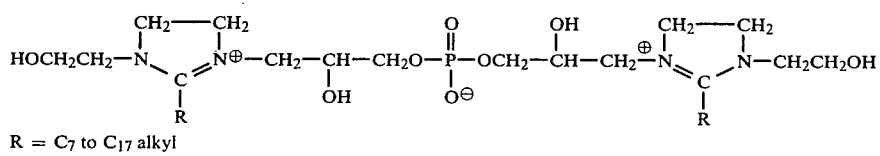

R = $C_7$ to $C_{17}$ alkyl

EXAMPLE 62

18.04 parts of Reactant "C" and 60.0 parts of water are charged into a suitable reaction vessel under good agitation. Heat is applied to 50° C. 21.96 parts of N-amidoethyl-N-hydroxyethyl-glycine (alkyl being 70% $C_{11}$ and 30% $C_{13}$) are charged under good agitation. Heating is continued to 90°–95° C. and the heated mixture held at this temperature for 4 hours. Reaction is complete when inorganic chloride reaches theoretical and residual 3° N. is vanishingly small.

The product is an aqueous solution of a novel product having the following structure:

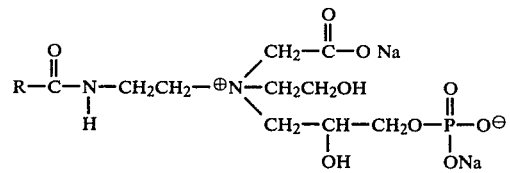

R = 70/30 Lauric/Myristic

EXAMPLE 63

25.6 parts of Reactant "D" and 60.0 parts water are charged into a suitable reaction vessel under good agitation. Heat is applied to 50° C. 14.4 parts of 1-hydroxyethyl-2-alkyl-2-imidazoline (alkyl having 7–17 carbons) are charged under good agitation. Heating is continued to 90°–95° C. and the heated mixture held at this temperature for 4 hours. Reaction reaches 97%

EXAMPLE 64

22.0 parts of Reactant "D" and 60.0 parts water are charged into a suitable reaction vessel under good agitation. Heat is applied to 50° C. 18.0 parts of 1-hydroxyethyl-2-alkyl-2-imidazoline (being $C_{17}$) are charged under good agitation. Heating is continued to 90°–95° C. and the heated mixture held at this temperature for 4 hours. Reaction reaches 97% during this time via inorganic chloride and tertiary amine analysis.

The product is an aqueous solution of a novel product having the following structure:

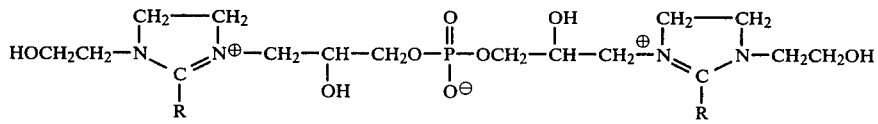

R = $C_{17}$ alkyl

EXAMPLE 65

24.2 parts of Reactant "D" and 60.0 parts water are charged into a suitable reaction vessel under good agitation. Heat is applied to 50° C. 15.8 parts of 1-hydroxyethyl-2-alkyl-2-imidazoline (being 70% $C_{11}$, 30% $C_{13}$) are charged under good agitation. Heating is continued to 90°–95° C. and the heated mixture held at this temperature for 4 hours. Reaction reaches 97% during this time via inorganic chloride and tertiary amine analysis.

The product is an aqueous solution of a novel product having the following structure:

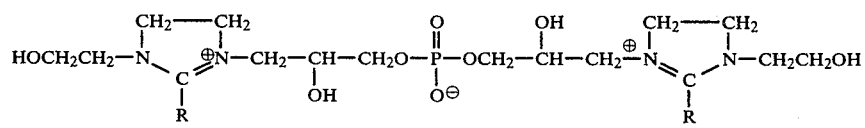

R = $C_{11}$ - 70% alkyl
$C_{13}$ - 30% alkyl

EXAMPLE 66

26.0 parts of Reactant "D" and 60.0 parts of water are charged into a suitable reaction vessel under good agitation. Heat is applied to 50° C. 14.0 parts of 1-hydroxyethyl-2-alkyl-2-imidazoline (being $C_{11}$) are charged under good agitation. Heating is continued to 90°–95° C. and the heated mixture held at this temperature for 4 hours. Reaction reaches 97% during this time via inorganic chloride and tertiary amine analysis.

The product is an aqueous solution of a novel product having the following structure:

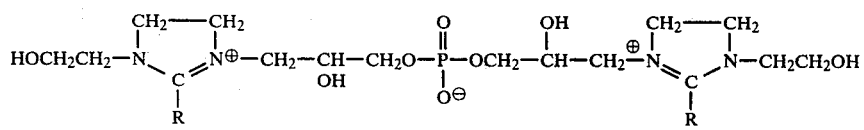

R = C$_{11}$ alkyl

EXAMPLE 67

28.5 parts of Reactant "D" and 60.0 parts water are charged into a suitable reaction vessel under good agitation. Heat is applied to 50° C. 11.5 parts of 1-hydroxethyl-2-alkyl-2-imidazoline (being C$_7$) are charged under good agitation. Heating is continued to 90°–95° C. and the heated mixture held at this temperature for 4 hours. Reaction reaches 97% during this time via inorganic chloride and tertiary amine analysis.

The product is an aqueous solution of a novel product having the following structure;

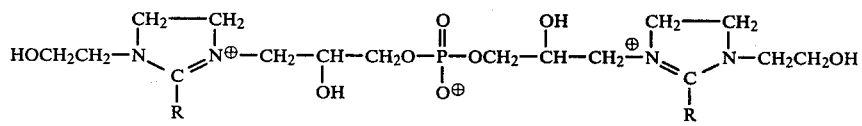

R = C$_7$ alkyl

EXAMPLE 68

22.61 parts of Reactant "H" and 60.0 parts of water are charged into a suitable reaction vessel under good agitation. Heat is applied to 50° C. 17.39 parts of 1-hydroxyethyl-2-alkyl-2-imidazoline (alkyl being C$_7$ to C$_{17}$) are charged under good agitation. Heating is continued to 90°–95° C. and the heated mixture held at this temperature for 4 hours. Reaction is complete when inorganic chloride reaches theoretical and residual 3° N. is vanishingly small.

The product is an aqueous solution of a novel product having the following structure:

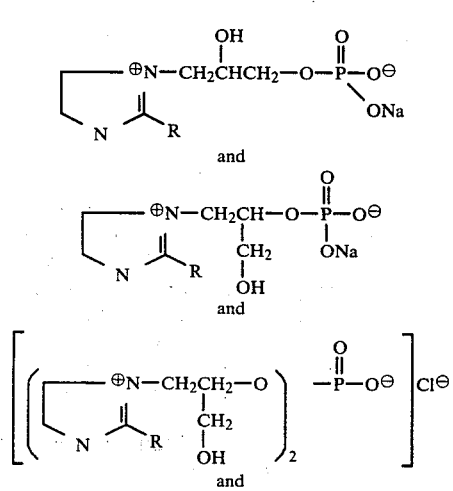

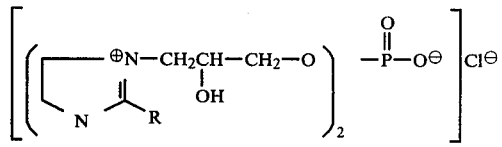

R = C$_7$ to C$_{17}$ alkyl

EXAMPLE 69

21.87 parts of Reactant "I" and 60.0 parts of water are charged into a suitable reaction vessel under good agitation. Heat is applied to 50° C. 18.13 parts of 1-hydroxyethyl-2-alkyl-2-imidazoline (alkyl being C$_7$ to C$_{17}$) are charged under good agitation. Heating is continued to 90°–95° C. and the heated mixture held at this temperature for 4 hours. Reaction is complete when inorganic chloride reaches theoretical and residual 3° N. is vanishingly small.

The product is an aqueous solution of a novel product having the following structure:

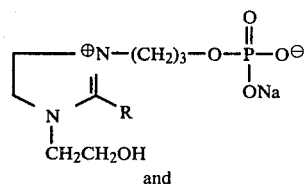

and

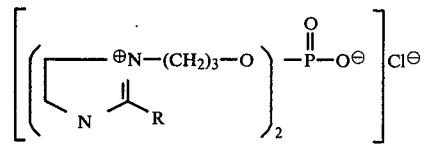

R - C$_7$ to C$_{17}$

EXAMPLE 70

20.53 parts of Reactant "G" and 60.0 parts of water are charged into a suitable reaction vessel under good agitation. Heat is applied to 50° C. 19.47 parts of 3-lauramidopropyl diethylamine are charged under good agitation. Heating is continued to 90°–95° C. and the heated mixture held at this temperature for 4 hours. Reaction is complete when inorganic chloride reaches theoretical and residual 3° N. is vanishingly small.

The product is an aqueous solution of a novel product having the following structure:

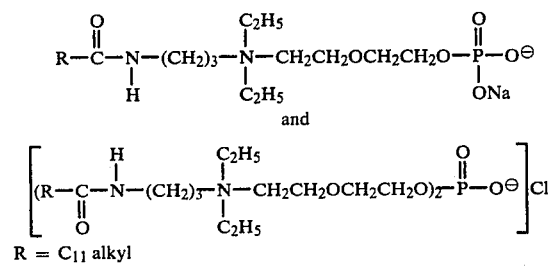

R = C₁₁ alkyl

EXAMPLE 71

21.47 parts of Reactant "G" and 60.0 parts of water are charged into a suitable reaction vessel under good agitation. Heat is applied to 50° C. 18.53 parts of 3-lauramidopropyl dimethylamine are charged under good agitation. Heating is continued to 90°–95° C. and the heated mixture held at this temperature for 4 hours. Reaction is complete when inorganic chloride reaches theoretical and residual 3° N. is vanishingly small.

The product is an aqueous solution of a novel product having the following structure:

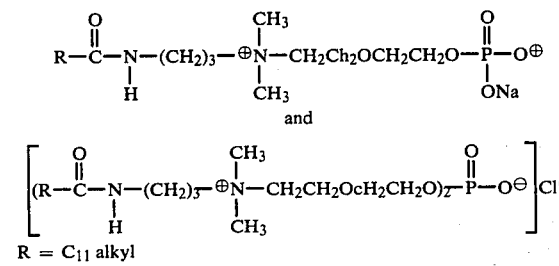

R = C₁₁ alkyl

EXAMPLE 72

21.00 parts of Reactant "H" and 60.0 parts of water are charged into a suitable reaction vessel under good agitation. Heat is applied to 50° C. 19.0 parts of 3-lauramidopropyl dimethylamine are charged under good agitation. Heating is continued to 90°–95° C. and the heated mixture held at this temperature for 4 hours. Reaction is complete when inorganic chloride reaches theoretical and residual 3° N. is vanishingly small.

The product is an aqueous solution of a novel product having the following structure:

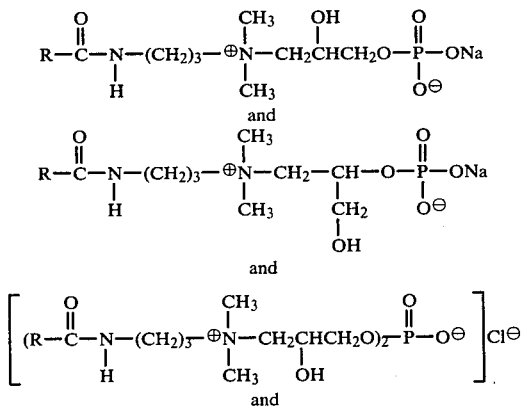

and

-continued

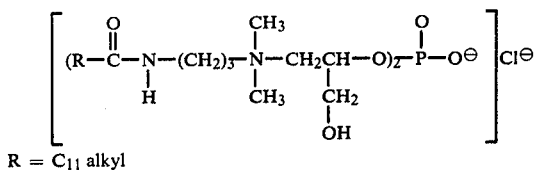

R = C₁₁ alkyl

EXAMPLE 73

18.29 parts of Reactant "C" and 60.0 parts of water are charged into a suitable reaction vessel under good agitation. Heat is applied to 50° C. 21.71 parts of N-alkylethyl-N-hydroxyethyl-glycine (alkyl being lauric) are charged under good agitation. Heating is continued to 90°–95° C. and the heated mixture held at this temperature for 4 hours. Reaction is complete when inorganic chloride reaches theoretical and residual 3° N. is vanishingly small.

The product is an aqueous solution of a novel product having the following structure:

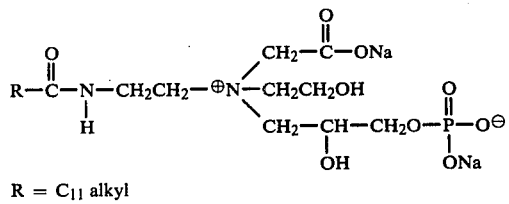

R = C₁₁ alkyl

EXAMPLE 74

17.48 parts of Reactant "C" and 60.0 parts of water are charged into a suitable reaction vessel under good agitation. Heat is applied to 50° C. 22.52 parts of N-alkylethyl-N-hydroxyethyl-glycine (alkyl being C₇ to C₁₇) are charged under good agitation. Heating is continued to 90°–95° C. and the heated mixture held at this temperature for 4 hours. Reaction is complete when inorganic chloride reaches theoretical and residual 3° N. is vanishingly small.

The product is an aqueous solution of a novel product having the following structure:

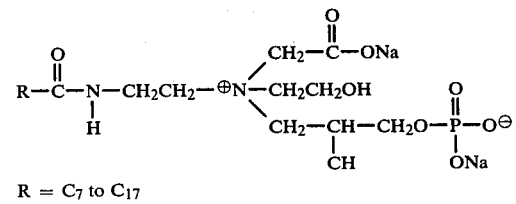

R = C₇ to C₁₇

EXAMPLE 75

18.73 parts of Reactant "B" and 60.0 parts of water are charged into a suitable reaction vessel under good agitation. Heat is applied to 50° C. 21.27 parts of N-alkylethyl-N-hydroxyethyl-glycine (alkyl being lauric) are charged under good agitation. Heating is continued to 90°–95° C. and the heated mixture held at this temperature for 4 hours. Reaction is complete when inorganic chloride reaches theoretical and residual 3° N. is vanishingly small.

The product is an aqueous solution of a novel product having the following structure:

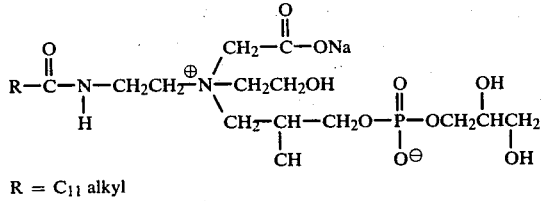

R = C₁₁ alkyl

EXAMPLE 76

12.69 parts of Reactant "D" and 60.0 parts of water are charged into a suitable reaction vessel under good agitation. Heat is applied to 50° C. 27.31 parts of N-alkylethyl-N-hydroxyethyl-glycine (alkyl being lauric) are charged under good agitation. Heating is continued to 90°-95° C. and the heated mixture held at this temperature for 4 hours. Reaction is complete when inorganic chloride reaches theoretical and residual 3° N. is vanishingly small.

The product is an aqueous solution of a novel product having the following structure:

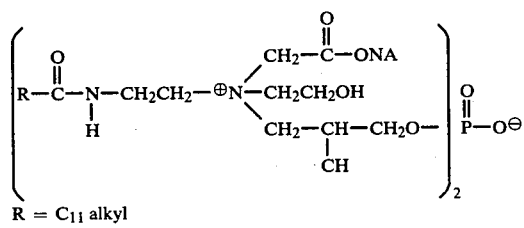

R = C₁₁ alkyl

EXAMPLE 77

15.73 parts of Reactant "A" and 60.0 parts of water are charged into a suitable reaction vessel under good agitation. Heat is applied to 50° C. 24.27 parts of N-alkylethyl-N-hydroxyethyl-glycine (alkyl being myristic) are charged under good agitation. Heating is continued to 90°-95° C. and the heated mixture held at this temperature for 4 hours. Reaction is complete when inorganic chloride reaches theoretical and residual 3° N. is vanishingly small.

The product is an aqueous solution of novel product having the following structure:

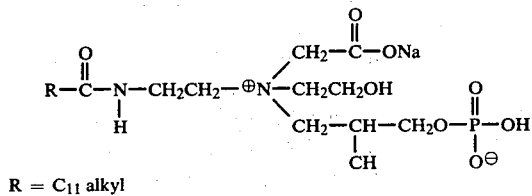

R = C₁₁ alkyl

PREPARATION OF REACTANT SPECIES

EXAMPLE 78

Reactant "A"

60.00 parts of deionized water are charged into a suitable reactor to which 22.58 parts of NaH₂PO₄ and 0.70 parts of NaOH are charged under good agitation. Mix well until a solution is obtained. 17.42 parts of Epichlorohydrin is charged under good agitation. The reactor is sealed and 5 PSIG N₂ is applied. Heat to 80°-85° C. holding the heated mixture at this temperature for 2 hours after the batch clears (approximately 3 hours total). Reaction is complete when theoretical reduction in acid value is obtained. Inorganic chloride will be less than 0.50%.

The product is an aqueous solution of a novel product having the following structure:

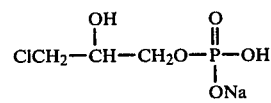

EXAMPLE 79

Reactant "B"

60.00 parts of deionized water are charged into a suitable reactor to which 17.37 parts of Na₂HPO₄ are charged. Mix well until a solution is obtained. 22.63 parts of Epichlorohydrin are charged under good agitation. The reactor is sealed and 5 PSIG N₂ is applied. Heat to 80°-85° C. holding the heated mixture at this temperature for approximately 2 hours after the batch clears (approximately 3 hours total). Reaction is complete when theoretical chloride is obtained and theoretical reduction in acid value is realized.

The product is an aqueous solution of a novel product having the following structure:

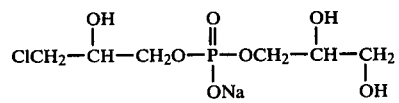

EXAMPLE 80

REACTANT "C"

60.00 parts of deionized water are charged into a suitable reactor to which 17.37 parts of Na₂HPO₄ are charged. Mix well until a solution is obtained. 22.63 parts of Epichlorohydrin are charged under good agitation. The reactor is sealed and 5 PSIG N₂ is applied. Heat to 80°-85° C. holding the heated mixture at this temperature for 2 hours after the batch clears (approximately 3 hours total). Reaction is complete when theoretical reduction in acid value and theoretical inorganic chloride values are obtained.

The product is an aqueous solution of a novel product having the following structure:

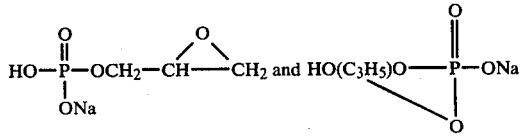

EXAMPLE 81

REACTANT "D"

60.00 parts of deionized water are charged into a suitable reactor to which 17.09 parts of NaH₂PO₄ and 0.70 parts of NaOH are charged. Mix well until a solution is achieved. 22.91 parts of Epichlorohydrin is charged under good agitation. Reactor is sealed and 5 PSIG N₂ is applied. Heat is applied to approximately 80°-85° C. and the heated mixture held at this temperature for approximately 3 hours after the batch clears (approximately 5 hours total). Reaction is complete when acid value is reduced by the theoretical amount. Inorganic chloride will be less than 0.5%.

The product is an aqueous solution of a novel product having the following structure:

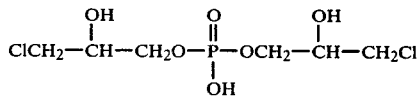

EXAMPLE 82
REACTANT "E"

48.79 parts of 2-chloroethanol is slowly charged into 51.21 parts of polyphosphoric acid under good agitation. The mixture is slowly heated to 90°–95° C. and held at this temperature for approximately 2 hours. Reaction is complete when theoretical reduction in acid value is obtained. 35.67 parts of the above product are mixed with 55.14 parts of deionized water. 8.32 parts of NaOH is slowly charged. Reaction is complete when theoretical acid value is obtained.

The product is an aqueous solution of a novel product having the following structure:

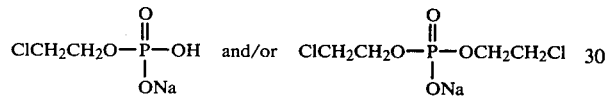

EXAMPLE 83
REACTANT "F"

66.17 parts of 1-chloro-2-propanol are slowly charged to 33.83 parts of polyphosphoric acid under good agitation.

Heat slowly to 90°–95° C. holding the heated mixture at this temperature for approximately 2 hours. Reaction is complete when theoretical reduction in acid value is obtained. 34.90 parts of the above are mixed with 60.00 parts soft water. 5.10 parts NaOH are slowly added. Reaction is complete when theoretical reduction in acid value is achieved.

The product is an aqueous solution of a novel product having the following structure:

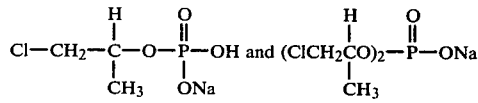

It will be understood that the specification and examples are illustrative but not limitative of the present invention and that other embodiments within the spirit and scope of the invention will suggest themselves to those skilled in the art.

EXAMPLE 84
REACTANT "G"

69.60 parts of 2-[2-(2-chloroethoxy-ethoxy)] ethanol are slowly charged to 30.40 parts of polyphosphoric acid under good agitation. Heat slowly to 90°–95° C. holding the heated mixture at this temperature for approximately 2 hours. Reaction is complete when theoretical reduction in acid value is obtained. 35.36 parts of the above are mixed with 60.00 parts soft water. 4.64 parts NaOH are slowly added. Reaction is complete when theoretical reduction in acid value is achieved.

The product is an aqueous solution of a novel product having the following structure:

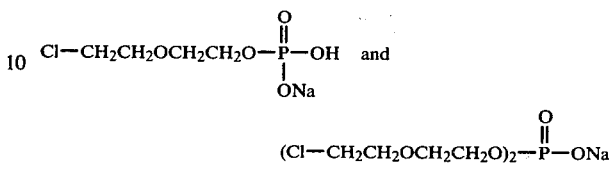

EXAMPLE 85
REACTANT "H"

68.09 parts of 3-chloro-1,2-propanediol are slowly charged to 31.91 parts of polyphosphoric acid under good agitation. Heat slowly to 90°–95° C. holding the heated mixture at this temperature for approximately 2 hours. Reaction is complete when theoretical reduction in acid value is obtained. 35.17 parts of the above are mixed with 60.00 parts soft water. 4.83 parts NaOH are slowly added. Reaction is complete when theoretical reduction in acid value is achieved.

The product is an aqueous solution of a novel product having the following structure:

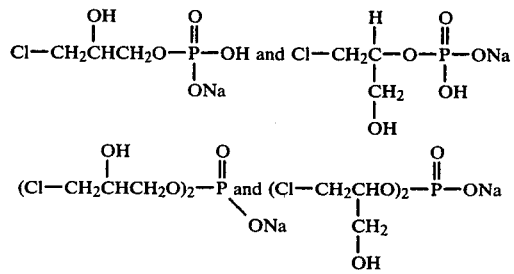

EXAMPLE 86
REACTANT "I"

66.17 parts of 1-chloro-3-hydroxy-propane are slowly charged to 33.83 parts of polyphosphoric acid under good agitation. Heat slowly to 90°–95° C. holding the heated mixture at this temperature for approximately 2 hours. Reaction is complete when theoretical reduction in acid value is obtained. 35.44 parts of the above are mixed with 60.00 parts soft water. 4.56 parts NaOH are slowly added. Reaction is complete when theoretical reduction in acid value is achieved.

The product is an aqueous solution of a novel product having the following structure:

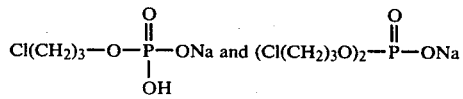

What is claimed is:
1. Phosphobetaine compounds of the formula

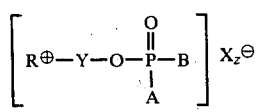 (I)

wherein
A is selected from O⁻, OM, and —O—Y—R⁺
B is selected from O⁻ and OM'
X⁻ is an anion
z is an integer from 0 to 2
with the proviso that only one of A and B can be O⁻ and z is of a value necessary for charge balance;
R is an amidoamine reactant moiety of the formula

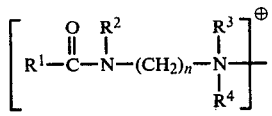

wherein
$R^1$ is alkyl, alkenyl, alkoxy, or hydroxyalkyl of from 5 to 22 carbon atoms each, or aryl or alkaryl of up to 20 carbon atoms,
$R^2$ is hydrogen or alkyl, hydroxyalkyl or alkenyl of up to 6 carbon atoms each or cycloalkyl of up to 6 carbon atoms, preferably of from 2 to 5 carbon atoms, or polyoxyalkalene of up to 10 carbon atoms,
$R^3$ and $R^4$, which may be the same or different, are selected from alkyl, hydroxyalkyl, carboxyalkyl of up to 6 carbon atoms in each alkyl moiety, and polyoxyalkylene of up to 10 carbon atoms; in addition, $R^3$ and $R^4$ taken together with the nitrogen to which they are attached, may represent an N-heterocycle, e.g., a morpholino structure, in which the Y radical is bonded to a ring atom of said N-heterocycle other than the nitrogen of the R moiety;
n is an integer from 2 to 12; Y is alkylene, optionally interrupted by up to 3 oxygen atoms, of up to 12 carbon atoms, which alkylene chain may optionally be substituted with lower alkyl, alkoxy, hydroxy or hydroxyalkyl, e.g. of not more than 10 carbon atoms each;
M and M', which may be the same or different, are (a) hydrogen, (b) an organic radical selected from alkyl or hydroxyalkyl of up to 6 carbon atoms, polyhydroxyalkyl of up to 10 carbon atoms, glyceryl, cycloalkyl of up to 6 carbon atoms, aryl or arylalkyl of up to 10 carbon atoms, or (c) a salt radical selected from alkali metals, alkaline earth metals, and mono-, di-, or tri-ethanolamine, provided that when either M or M' is an organic radical (b), the other M and M' must be hydrogen or a salt radical (c).

2. Phosphobetaine compound as claimed in claim 1, of the formula

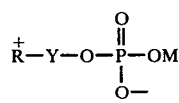

wherein the R, Y amd M radicals are defined as before.

3. Phosphobetaine as claimed in claim 1, of the formula

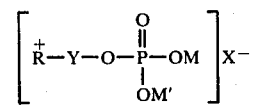

wherein the R, Y, M, M' and X radicals are defined as before.

4. Phosphobetaine as claimed in claim 1, of the formula

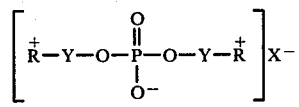

wherein the R, Y and X radicals are defined as before.

5. Phosphobetaine compounds as claimed in claim 2, wherein R is an amidoamine reactant moiety of the formula

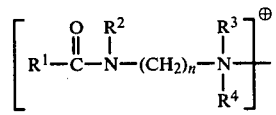

wherein
$R^1$ is alkyl, alkenyl, alkoxy, or hydroxyalkyl of from 5 to 22 carbon atoms each, or aryl or alkaryl of up to 20 carbon atoms,
$R^2$ is hydrogen or alkyl, hydroxyalkyl or alkenyl of up to 6 carbon atoms each or cycloalkyl of up to 6 carbon atoms, preferably of from 2 to 5 carbon atoms, or polyoxyalkalene of up to 10 carbon atoms,
$R^3$ and $R^4$, which may be the same or different, are selected from alkyl, hydroxyalkyl, carboxyalkyl of up to 6 carbon atoms in each alkyl moiety, and polyoxyalkylene of up to 10 carbon atoms; in addition, $R^3$ and $R^4$ taken together with the nitrogen to which they are attached, may represent an N-heterocycle, e.g., a morpholino structure, in which the Y radical is bonded to a ring atom of said N-heterocycle other than the nitrogen of the R moiety;
n is an integer from 2 to 12.

6. Phosphobetaine compound as claimed in claim 3, wherein
R is

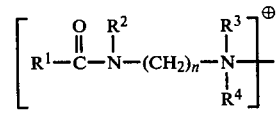

wherein
$R^1$ is alkyl, alkenyl, alkoxy, or hydroxyalkyl of from 5 to 22 carbon atoms each, or aryl or alkaryl of up to 20 carbon atoms,
$R^2$ is hydrogen or alkyl, hydroxyalkyl or alkenyl of up to 6 carbon atoms each or cycloalkyl of up to 6 carbon atoms, preferably of from 2 to 5 carbon atoms, or polyoxyalkalene of up to 10 carbon atoms, R[3] and R[4], which may be the same or different, are selected from alkyl, hydroxyalkyl, carboxyalkyl of up to 6 carbon atoms in each alkyl moiety, and polyoxyalkylene of up to 10 carbon atoms; in addition, R[3] and R[4] taken together with the nitrogen to which they are attached, may represent an N-heterocycle, e.g., a morpholino structure, in which the Y radical is bonded to a ring atom of said N-heterocycle other than the nitrogen of the R moiety;

n is an integer from 2 12.

7. Phosphobetaine compound as claimed in claim 4, wherein

R is

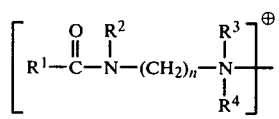

wherein

R[1] is alkyl, alkenyl, alkoxy, or hydroxyalkyl of from 5 to 22 carbon atoms each, or aryl or alkaryl of up to 20 carbon atoms, R[2] is hydrogen or alkyl, hydroxyalkyl or alkenyl of up to 6 carbon atoms each or cycloalkyl of up to 6 carbon atoms, preferably of from 2 to 5 carbon atoms, or polyoxyalkalene of up to 10 carbon atoms, R[3] and R[4], which may be the same or different, are selected from alkyl, hydroxyalkyl, carboxyalkyl of up to 6 carbon atoms in each alkyl moiety, and polyoxyalkylene of up to 10 carbon atoms; in addition, R[3] and R[4] taken together with the nitrogen to which they are attached, may represent an N-heterocycle, e.g., a morpholino structure, in which the Y radical is bonded to a ring atom of said N-heterocycle other than the nitrogen of the R moiety;

n is an integer from 2 to 12.

8. Phosphobetaine compound as claimed in claim 2, wherein

M is hydrogen.

9. Phosphobetaine compound as claimed in claim 2, wherein

M is an organic radical selected from alkyl or hydroxyalkyl of up to 6 carbon atoms, polyhydroxyalkyl of up to 10 carbon atoms, glyceryl, cycloalkyl of up to 6 carbon atoms, aryl or arylalkyl of up to 10 carbon atoms.

10. Phosphobetaine compound as claimed in claim 2, wherein

M is a salt radical selected from alkali metals, alkaline earth metals, alkaline earth metals and mono-, di-, or tri-ethanolamine.

11. Phosphobetaine compound as claimed in claim 3, wherein one of M and M' is hydrogen.

12. Phosphobetaine compound as claimed in claim 3, wherein one of M and M' is an organic radical selected from alkyl or hydroxyalkyl of up to 6 carbon atoms, polyhydroxyalkyl of up to 10 carbon atoms, glyceryl, cycloalkyl of up to 6 carbon atoms, aryl or arylalkyl of up to 10 carbon atoms.

13. Phosphobetaine compound as claimed in claim 3, wherein one of M and M' is a salt radical selected from alkali metals, alkaline earth metals alkaline earth metals and mono-, di-, or tri-ethanolamine.

14. Phosphobetaine compound as claimed in claim 1, wherein said compound is lauric myristic amido 3-hydroxypropyl phosphobetaine.

15. Phosphobetaine compound as claimed in claim 1, wherein said compound is cocamido disodium 3-hydroxypropyl phosphobetaine.

16. Phosphobetaine compound as claimed in claim 1, wherein said compound is lauric myristic amido monosodium 3-hydroxypropyl phosphobetaine.

17. Phosphobetaine compound as claimed in claim 1, wherein said compound is lauric myristic amido disodium 3-hydroxypropyl phosphobetaine.

18. Phosphobetaine compound as claimed in claim 1, wherein said compound is lauric myristic amido glyceryl phosphobetaine.

19. Phosphobetaine compound as claimed in claim 1, wherein said compound is lauric myristic amido carboxy disodium 3-hydroxypropyl phosphobetaine.

* * * * *